(12) United States Patent
Horiuchi et al.

(10) Patent No.: US 12,727,854 B2
(45) Date of Patent: Sep. 8, 2026

(54) IMAGING TABLE, ULTRASONOGRAPHY APPARATUS, MAMMOGRAPHY APPARATUS, AND CONTROL PROGRAM

(71) Applicant: FUJIFILM Corporation, Tokyo (JP)

(72) Inventors: Hisatsugu Horiuchi, Kanagawa (JP); Lisako Nobuyama, Kanagawa (JP); Keiji Tsubota, Kanagawa (JP); Takeyasu Kobayashi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/590,886

(22) Filed: Feb. 28, 2024

(65) Prior Publication Data

US 2024/0293102 A1 Sep. 5, 2024

(30) Foreign Application Priority Data

Mar. 2, 2023 (JP) ................................ 2023-032234

(51) Int. Cl.
*A61B 8/00* (2006.01)
*A61B 8/08* (2006.01)

(52) U.S. Cl.
CPC ............ *A61B 8/403* (2013.01); *A61B 8/0825* (2013.01); *A61B 8/4209* (2013.01); *A61B 8/54* (2013.01)

(58) Field of Classification Search
CPC ......... A61B 8/0825; A61B 8/14; A61B 8/403; A61B 8/406; A61B 8/4209; A61B 8/4281; A61B 8/4405; A61B 8/54
See application file for complete search history.

(56) References Cited

U.S. PATENT DOCUMENTS

2004/0249271 A1* 12/2004 Besson ................ A61B 6/5247 600/437
2015/0119682 A1 4/2015 Nagae et al.
2015/0268091 A1 9/2015 Abe
2018/0080813 A1 3/2018 Abe
2019/0150895 A1* 5/2019 Tian ..................... A61B 8/4209
(Continued)

FOREIGN PATENT DOCUMENTS

CN 110613478 A * 12/2019 ............. A61B 8/488
CN 215191674 U * 12/2021
(Continued)

OTHER PUBLICATIONS

Translated Tangquin CN 110613478 (Year: 2019).*
Translated Zhang CN215191574U (Year: 2021).*

*Primary Examiner* — Brooke Lyn Klein
(74) *Attorney, Agent, or Firm* — Studebaker Brackett PLLC

(57) ABSTRACT

An object is to capture an ultrasound image from a contact surface of a breast in contact with an imaging table. There is provided an imaging table including: a space that is provided below a loading surface on which a breast is placed and is provided to dispose an ultrasound probe which outputs an ultrasonic wave from an outside of the loading surface toward the loading surface and acquires a reflected wave of the ultrasonic wave by the breast; and a contact surface with an acoustic matching member that is provided on a back surface of the loading surface and reduces a difference in acoustic impedance between the breast and the ultrasound probe.

5 Claims, 16 Drawing Sheets

(56) References Cited

U.S. PATENT DOCUMENTS

| | | | | |
|---|---|---|---|---|
| 2019/0175144 | A1* | 6/2019 | O'Brien | A61B 8/0816 |
| 2020/0305836 | A1* | 10/2020 | Arai | A61B 8/4416 |
| 2020/0405251 | A1* | 12/2020 | Long | A61B 6/502 |

FOREIGN PATENT DOCUMENTS

| | | | |
|---|---|---|---|
| JP | 2007-282960 | A | 11/2007 |
| JP | 2015-085201 | A | 5/2015 |
| JP | 2015-177907 | A | 10/2015 |

* cited by examiner 10A
13
10C
11
X
Y
Z
W
10B
10

IMAGING TABLE, ULTRASONOGRAPHY APPARATUS, MAMMOGRAPHY APPARATUS, AND CONTROL PROGRAM

CROSS REFERENCE TO RELATED APPLICATIONS

This application claims priority from Japanese Application No. 2023-032234, filed on Mar. 2, 2023, the entire disclosure of which is incorporated herein by reference.

BACKGROUND

1. Technical Field

The present disclosure relates to an imaging table, an ultrasonography apparatus, a mammography apparatus, and a non-transitory storage medium storing a control program.

2. Related Art

An ultrasonography apparatus that captures an ultrasound image of a breast by scanning a breast of an examinee with an ultrasound probe.

JP2015-85201A discloses a subject information acquisition device that acquires information of a subject by receiving an acoustic wave from the subject. In the device, a support body that supports a plurality of first conversion elements includes a bowl portion having a spherical surface, and a plurality of second conversion elements transmit acoustic waves and receive reflected waves in a space inside the spherical surface.

JP2015-177907A discloses a subject information acquisition device that acquires information of a subject by receiving an acoustic wave from the subject. The device includes a detector provided in a spherical shape such that directivity of a desired number of capacitive micro-machined ultrasound transducer (CMUT) probes is directed toward a center of a sphere, and acoustic waves are transmitted and reflected waves are received in a space inside the spherical surface.

JP2007-282960A discloses an ultrasound breast examination device that includes an ultrasound array probe, a liquid-filled container which contains a liquid and the ultrasound array probe and includes a stretchable membrane partially transmitting ultrasonic waves, and an ultrasound transceiver circuit that causes the ultrasound array probe to transmit and receive ultrasonic waves.

In a case of capturing an ultrasound image of a breast, an ultrasound image may be captured in a state where the breast of an examinee is placed on an imaging table. In this case, the ultrasound probe cannot be brought close to a breast portion in contact with the imaging table. As a result, an ultrasound image of the breast portion in contact with the imaging table may be unclear as compared with ultrasound images of other breast portions.

SUMMARY

The present disclosure has been made in view of the above circumstances, and an object of the present disclosure is to provide an imaging table, an ultrasonography apparatus, a mammography apparatus, and a non-transitory storage medium storing a program capable of capturing an ultrasound image from a contact surface of a breast in contact with an imaging table.

According to a first aspect, there is provided an imaging table including: a space that is provided below a loading surface on which a breast is placed and is provided to dispose an ultrasound probe which outputs an ultrasonic wave from an outside of the loading surface toward the loading surface and acquires a reflected wave of the ultrasonic wave by the breast; and a contact surface with an acoustic matching member that is provided on a back surface of the loading surface and reduces a difference in acoustic impedance between the breast and the ultrasound probe.

According to a second aspect, in the imaging table according to the first aspect, an attachment mechanism that attaches a fixing member for fixing the imaging table to an attachment portion of the imaging table is provided at each of a side surface intersecting the loading surface in front of a center of the loading surface and a side surface intersecting the loading surface on a far side from the center of the loading surface in a case of being viewed from an examinee whose the breast is placed on the loading surface such that a position of the loading surface does not change even in a case where the ultrasound probe is pressed against the back surface of the loading surface via the acoustic matching member.

According to a third aspect, in the imaging table according to the second aspect, the contact surface is protruded or recessed with respect to a peripheral surface of the contact surface.

According to a fourth aspect, in the imaging table according to the third aspect, in a case where the acoustic matching member in contact with the contact surface is jelly, the acoustic matching member is fixed to the contact surface by a holding member that attaches the acoustic matching member to the contact surface.

According to a fifth aspect, there is provided an ultrasonography apparatus including: the imaging table according to any one of the first aspect to the fourth aspect that is attached to the ultrasonography apparatus; and a controller that performs control to capture an ultrasound image of a breast by using a reflected wave of an ultrasonic wave, the reflected wave being acquired by the ultrasound probe.

According to a sixth aspect, the ultrasonography apparatus according to the fifth aspect further includes: a movement mechanism that moves the ultrasound probe in the space formed by the imaging table. In the ultrasonography apparatus, the controller controls a length of the ultrasound probe such that the ultrasound probe does not come into contact with a back surface of the loading surface of the imaging table in a case where the ultrasound probe is moved by using the movement mechanism, controls a length of the ultrasound probe such that the ultrasound probe comes into contact with the back surface of the loading surface of the imaging table via the acoustic matching member in a case where the ultrasound probe is moved to a predetermined position, and performs control of acquiring an ultrasound image at the predetermined position of the breast placed on the loading surface of the imaging table.

According to a seventh aspect, the ultrasonography apparatus according to the fifth aspect further includes: a movement mechanism that moves the ultrasound probe in the space formed by the imaging table. In the ultrasonography apparatus, the controller moves the ultrasound probe in a state where the ultrasound probe is in contact with a back surface of the loading surface of the imaging table via the acoustic matching member, and performs control of acquiring an ultrasound image of the breast placed on the loading surface of the imaging table.

According to an eighth aspect, in the ultrasonography apparatus according to the seventh aspect, a sliding plate that scrapes off the acoustic matching member while spreading the acoustic matching member on the back surface of the loading surface of the imaging table in a movement direction of the ultrasound probe is attached to the ultrasound probe.

According to a ninth aspect, in the ultrasonography apparatus according to the eighth aspect, in a case where the ultrasound probe is moved from a first point to a second point, the controller performs control of separating the ultrasound probe from the back surface of the loading surface of the imaging table at the second point such that the ultrasound probe is not brought into contact with an acoustic matching member pool, which is formed in front of the ultrasound probe in the movement direction by the acoustic matching member scraped off from the back surface of the loading surface of the imaging table due to movement of the ultrasound probe, moving the ultrasound probe to a position passing over the acoustic matching member pool, bringing the ultrasound probe into contact with the back surface of the loading surface of the imaging table, and moving the ultrasound probe toward the first point again.

According to a tenth aspect, in the ultrasonography apparatus according to the ninth aspect, in a case where imaging other than capturing of an ultrasound image is performed on the breast placed on the loading surface of the imaging table, the controller performs control of moving the ultrasound probe outside an imaging range of the other imaging.

According to an eleventh aspect, the ultrasonography apparatus according to the fifth aspect further includes: an imaging device that images the ultrasound probe in the space in a case where an opening portion for allowing a medical worker to insert his/her hand into the space and to move the ultrasound probe is provided at at least one of side surfaces intersecting a side surface facing a chest wall, among side surfaces of the imaging table that intersect the loading surface of the imaging table. In the ultrasonography apparatus, the controller performs control of acquiring an ultrasound image of the breast placed on the loading surface of the imaging table while displaying an image obtained from the imaging device on a display device.

According to a twelfth aspect, there is provided a mammography apparatus including: the ultrasonography apparatus according to the fifth aspect.

According to a thirteenth aspect, there is provided a mammography apparatus including: the ultrasonography apparatus according to any one of the fifth aspect to the eleventh aspect.

According to a fourteenth aspect, there is provided a non-transitory storage medium storing a program that causes a computer to execute a control process. the control process including: processing of performing control to capture an ultrasound image of a breast placed on a loading surface of an imaging table by causing an ultrasound probe to output an ultrasonic wave toward the loading surface and to acquire a reflected wave of the ultrasonic wave by the breast, the ultrasound probe being allowed to be disposed in a space that is provided below the loading surface.

According to the present disclosure, it is possible to capture an ultrasound image from a contact surface of a breast in contact with an imaging table.

BRIEF DESCRIPTION OF THE DRAWINGS

FIG. 9 is a diagram illustrating an example of an ultrasound probe that moves along a back surface of the imaging table.

FIG. 10 is a flowchart illustrating an example of a flow of imaging processing executed by the ultrasonography apparatus.

DESCRIPTION OF EMBODIMENTS

Figure 1:
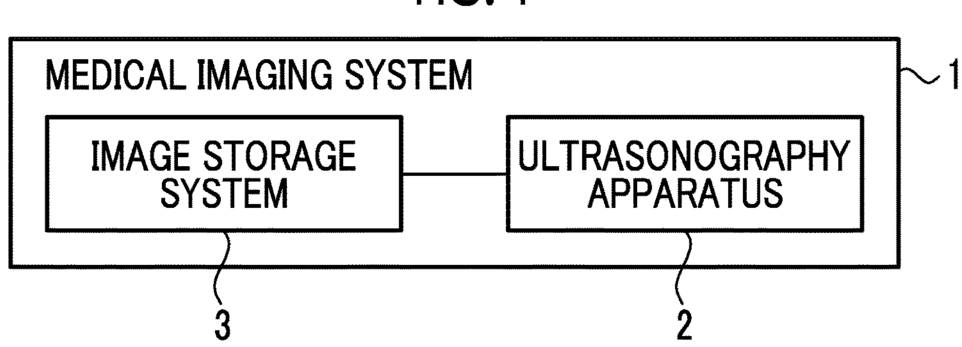
FIG. 1 is a diagram illustrating a configuration example of a medical imaging system according to a first embodiment.

Hereinafter, exemplary embodiments of the present invention will be described in detail with reference to the drawings. The identical components and the identical processes are denoted by the identical reference numerals throughout the drawings, and redundant description will be omitted.

First Embodiment

FIG. 1 is a diagram illustrating a configuration example of a medical imaging system 1 according to a first embodiment.

The medical imaging system 1 includes an ultrasonography apparatus 2 and an image storage system 3.

The ultrasonography apparatus 2 is an apparatus that captures an ultrasound image of a breast of an examinee as a subject by, for example, a medical worker such as an examination technician or a doctor.

The image storage system 3 is a system that stores the ultrasound images captured by the ultrasonography apparatus 2. The image storage system 3 extracts an ultrasound image corresponding to a request from the ultrasonography apparatus 2 or a console 6 (refer to FIG. 18) to be described later, from the stored ultrasound images, and transmits the extracted ultrasound image to a request source apparatus. A specific example of the image storage system 3 is a picture archiving and communication system (PACS).

Figure 2:
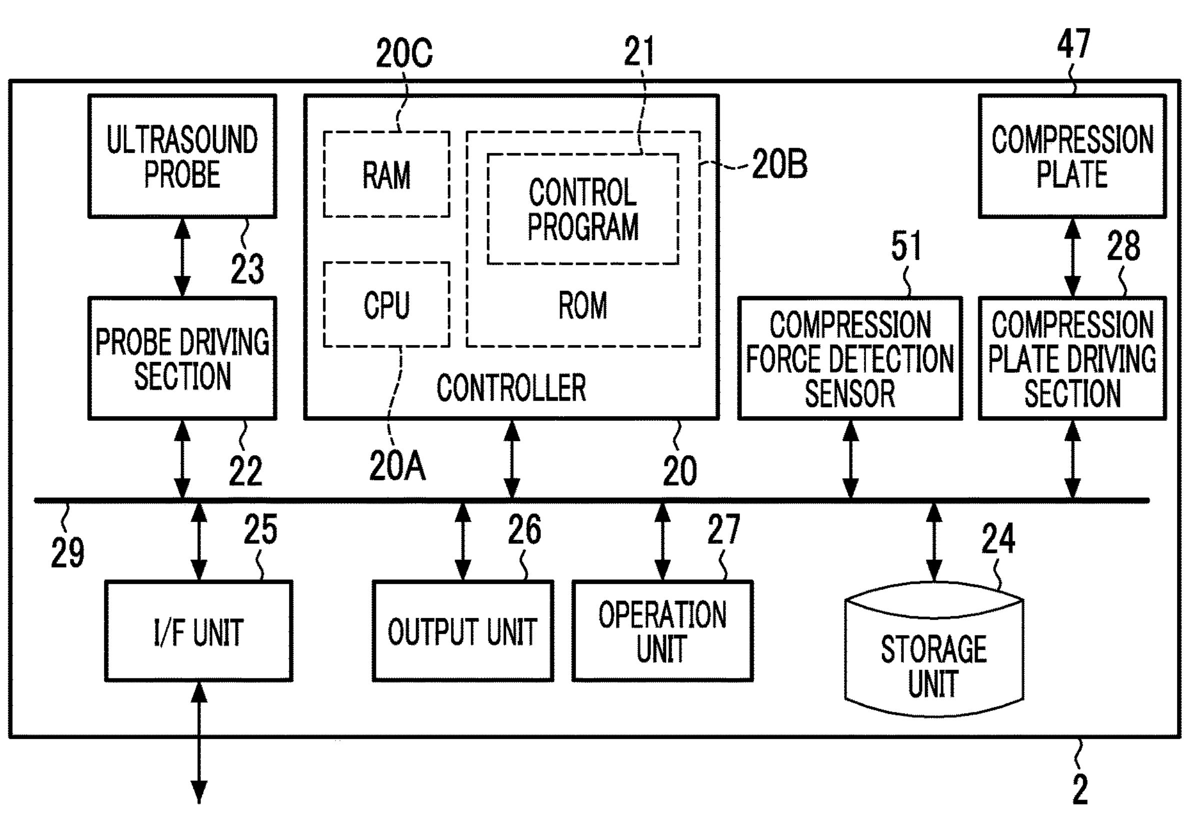
FIG. 2 is a diagram illustrating a configuration example of an ultrasonography apparatus.

First, a configuration example of the ultrasonography apparatus 2 will be described. FIG. 2 is a diagram illustrating a configuration example of the ultrasonography apparatus 2.

As illustrated in FIG. 2, the ultrasonography apparatus 2 includes a controller 20, a probe driving section 22, an ultrasound probe 23, a storage unit 24, an interface (I/F) unit 25, an output unit 26, an operation unit 27, a compression plate driving section 28, a compression plate 47, and a compression force detection sensor 51. The controller 20, the probe driving section 22, the storage unit 24, the I/F unit 25, the output unit 26, the operation unit 27, the compression plate driving section 28, and the compression force detection sensor 51 are connected to each other via a bus 29 to exchange various types of information.

The controller 20 controls an operation of the ultrasonography apparatus 2 based on an instruction from the medical worker. The controller 20 includes a central processing unit (CPU) 20A which is an example of a processor, a read only memory (ROM) 20B, and a random access memory (RAM) 20C. The ROM 20B stores in advance various programs including a control program 21 that is read by the CPU 20A to perform control for capturing an ultrasound image, and various parameters to be referred to in a case where the CPU 20A controls an operation of the ultrasonography apparatus 2. The RAM 20C is used as a temporary work area of the CPU 20A.

The ultrasound probe 23 outputs an ultrasonic wave to the subject, that is, the breast, acquires a reflected wave of the ultrasonic wave that is reflected by the breast, converts the acquired reflected wave into reflected wave data, and outputs the reflected wave data to the controller 20. The controller 20 that receives the reflected wave data generates an ultrasound image of the breast by using the reflected wave data which is received.

The probe driving section 22 causes the ultrasound probe 23 to move in a direction along a chest wall of the examinee in a case where the breast is viewed from above, that is, in a lateral direction, and in a direction intersecting the chest wall of the examinee, that is, in a vertical direction under a control of the controller 20. The medical worker may capture an ultrasound image of the breast by moving the ultrasound probe 23 held in the hand. Here, as an example, a position of the ultrasound probe 23 is changed by the probe driving section 22.

The compression plate 47 is a device that compresses a breast by pressing the breast from above. Preferably, the compression plate 47 has transparency such that a compressed state of the breast can be visually recognized.

The compression plate driving section 28 moves the compression plate 47 in an upward-downward direction under a control of the controller 20.

The compression force detection sensor 51 has a function of detecting a compression force of the compression plate 47 moved by driving of the compression plate driving section 28 against the breast.

As described above, the ultrasonography apparatus 2 captures an ultrasound image of the breast compressed by the compression plate 47. On the other hand, an ultrasound image of the breast can be captured without compressing the breast. For this reason, the ultrasonography apparatus 2 does not necessarily include the compression plate driving section 28, the compression plate 47, and the compression force detection sensor 51.

The storage unit 24 stores the captured ultrasound images, various information, and the like. The storage unit 24 is an example of a storage device that maintains stored information even in a case where power supplied to the storage unit 24 is cut off. For example, a semiconductor memory such as a solid state drive (SSD) is used, or a hard disk may be used.

The I/F unit 25 transmits and receives various kinds of information to and from an external apparatus connected to a communication line (not illustrated) such as a local area network (LAN), by using wireless communication or wired communication. For example, the controller 20 transmits the captured ultrasound image to the image storage system 3 via the I/F unit 25.

The output unit 26 outputs, to the medical worker, information processed by the controller 20 such as information related to the imaging status of the ultrasound image, the captured ultrasound image, and a warning. Outputting the information means presenting the information in a state where the medical worker can confirm the information. Therefore, for example, all of a form in which information is displayed on a display (not illustrated) that is an example of a display device, a form in which information is printed on a recording medium such as paper by an image forming apparatus (not illustrated), and a form in which information is notified by voice via a speaker (not illustrated) are examples of outputting information by the output unit 26.

The operation unit 27 is used by the medical worker to input, for example, instructions and various kinds of information related to capturing of an ultrasound image. An operation form of the operation unit 27 is not limited, and, for example, an operation by a switch, a touch panel, a touch pen, a mouse, or the like can be received.

Figure 3:
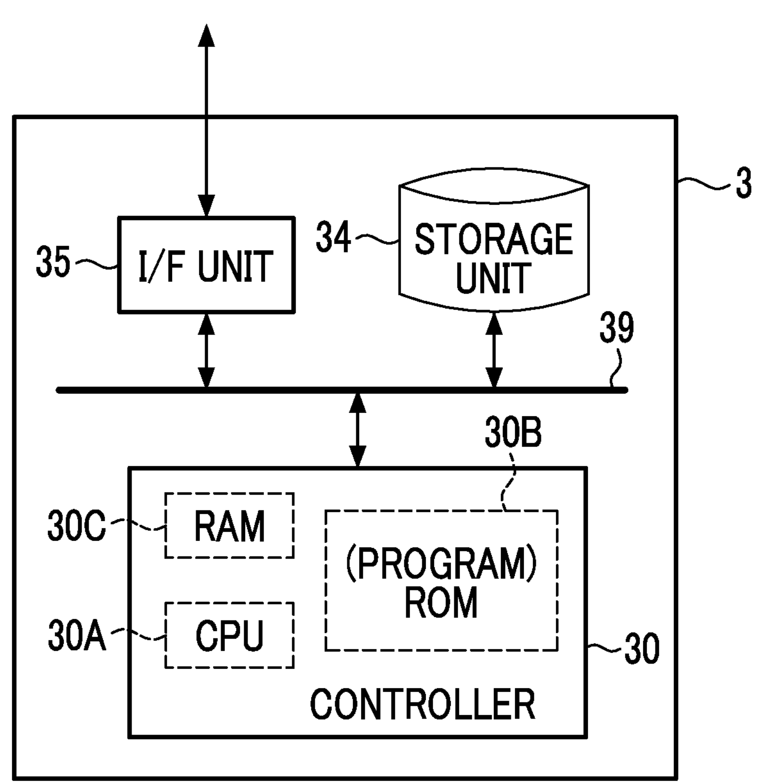
FIG. 3 is a diagram illustrating a configuration example of an image storage system.

On the other hand, FIG. 3 is a diagram illustrating a configuration example of the image storage system 3. As illustrated in FIG. 3, the image storage system 3 includes a controller 30, a storage unit 34, and an I/F unit 35. The controller 30, the storage unit 34, and the I/F unit 35 are connected to each other via a bus 39 such that various kinds of information can be exchanged.

The controller 30 controls an operation of the image storage system 3. The controller 30 includes a CPU 30A, a ROM 30B, and a RAM 30C. Various programs that are read by the CPU 30A to perform control related to storing of the ultrasound images and various parameters that are referred to by the CPU 30A to control an operation of the image storage system 3 are stored in the ROM 30B in advance. The RAM 30C is used as a temporary work area of the CPU 30A.

The storage unit 34 stores the ultrasound image in association with, for example, a capturing order or information related to the examinee. That is, the storage unit 34 functions as a database for the ultrasound images.

The I/F unit 35 transmits and receives various kinds of information to and from an external apparatus connected to a communication line such as a LAN, by using wireless communication or wired communication. For example, the controller 30 transmits a requested ultrasound image to the ultrasonography apparatus 2 via the I/F unit 35.

Figure 4:
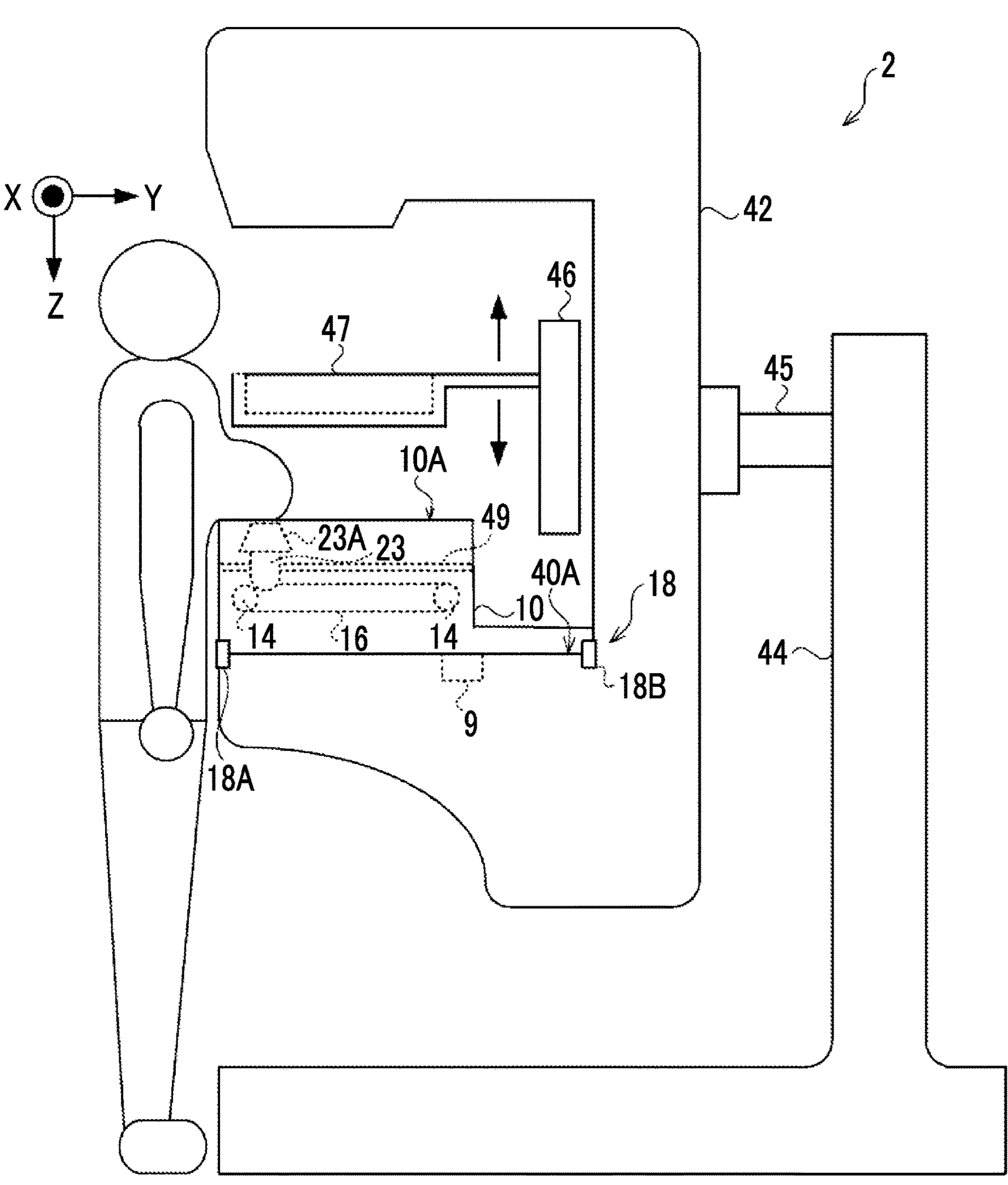
FIG. 4 is a diagram illustrating an example of an external appearance of the ultrasonography apparatus according to a first embodiment.

Next, an example of capturing of an ultrasound image of a breast by the ultrasonography apparatus 2 will be described. FIG. 4 is a diagram illustrating an example of an external appearance of the ultrasonography apparatus 2 according to the first embodiment in a case where the ultrasonography apparatus is viewed from a side.

The ultrasonography apparatus 2 includes an arm portion 42, a base 44, and a shaft portion 45. The arm portion 42 is held by the base 44 so as to be movable in an upward-downward direction (Z-axis direction). The shaft portion 45 connects the arm portion 42 to the base 44. The arm portion 42 can be relatively rotated with respect to the base 44, using the shaft portion 45 as a rotation axis.

The arm portion 42 is provided with a work table 40A on which work of capturing an ultrasound image is performed, a probe driving unit 9, and a compression plate driving unit 46.

The imaging table 10 is placed on the work table 40A, and the examinee places the breast on a loading surface 10A located on an upper surface of the imaging table 10.

The compression plate 47 is attached to the compression plate driving unit 46, and the compression plate driving unit 46 moves the compression plate 47 in a downward direction according to an instruction from the compression plate driving section 28. Thereby, the breast placed on the loading surface 10A of the imaging table 10 is pressed and compressed by the compression plate 47. In addition, the compression plate driving unit 46 moves the compression plate 47, which is compressing the breast, in an upward direction according to an instruction from the compression plate driving section 28. Thereby, the compression of the breast by the compression plate 47 is released.

For the movement direction of the compression plate 47, in particular, a direction in which the breast is compressed, that is, a direction in which the compression plate 47 approaches the loading surface 10A of the imaging table 10 may be referred to as a "compression direction", and a direction in which the compression of the breast is released, that is, a direction in which the compression plate 47 is moved away from the loading surface 10A of the imaging table 10 may be referred to as a "compression release direction".

The imaging table 10 includes a loading surface 10A on which the breast is placed and surfaces that intersect the loading surface 10A along the periphery of the loading surface 10A, that is, side surfaces of the imaging table 10. A surface facing the loading surface 10A, that is, a surface in contact with the worktable 40A is an open surface. A space is provided below the loading surface 10A, and is provided to dispose the ultrasound probe 23. In the imaging table 10 illustrated in FIG. 4, a height of the imaging table 10 along the Z-axis direction is divided into two stages, and an upper surface having a higher height is used as the loading surface 10A on which the breast is placed.

In the space of the imaging table 10, the ultrasound probe 23 which is attached such that an ultrasonic wave output port faces the loading surface 10A is provided. The ultrasound probe 23 acquires a reflected wave of the ultrasonic wave which is output from the outside of the loading surface 10A toward the loading surface 10A and is reflected by the breast. As will be described below, a sliding plate 23A is attached to the periphery of the ultrasonic wave output port of the ultrasound probe 23 so as to surround the ultrasonic wave output port.

In the space of the imaging table 10, a movement rail 49 is attached, for example, along a horizontal direction which is a direction along the chest wall of the examinee, that is, an X-axis direction, and a vertical direction which is a direction intersecting the chest wall of the examinee, that is, a Y-axis direction orthogonal to the X-axis direction and the Z-axis direction. The ultrasound probe 23 is attached to the movement rail 49, and moves in a direction along the movement rail 49 by using, as a driving force, movement of a belt 16 suspended between rollers 14 rotated by a motor (not illustrated). A movement mechanism for moving the ultrasound probe 23 is not limited, and a known moving method is applied. In addition, even in a case where a movement mechanism for moving the ultrasound probe 23 is not attached to the imaging table 10, the movement mechanism of the ultrasound probe 23 as a separate body may be accommodated in the space of the imaging table 10.

The probe driving unit 9 moves the ultrasound probe 23 to an instructed position by rotating the motor according to an instruction from the probe driving section 22.

The imaging table 10 is attached to the work table 40A by using fixing members 18 such that the position does not change even in a case where an impact is applied from the outside. Specifically, in a case where the imaging table 10 is viewed from the examinee whose breast is placed on the loading surface 10A of the imaging table 10, an attachment mechanism for attaching the fixing members 18 for fixing the imaging table 10 to the work table 40A is provided on each of the side surface of the imaging table 10 in front of the center of the loading surface 10A and the side surface of the imaging table 10 on a far side from the center of the loading surface 10A.

In the example illustrated in FIG. 4, the fixing member 18A is the fixing member 18 which is attached to the attachment mechanism on the side surface of the imaging table 10 in front of the center of the loading surface 10A, and the fixing member 18B is the fixing member 18 which is attached to the attachment mechanism on the side surface of the imaging table 10 on a far side from the center of the loading surface 10A.

Figure 5:
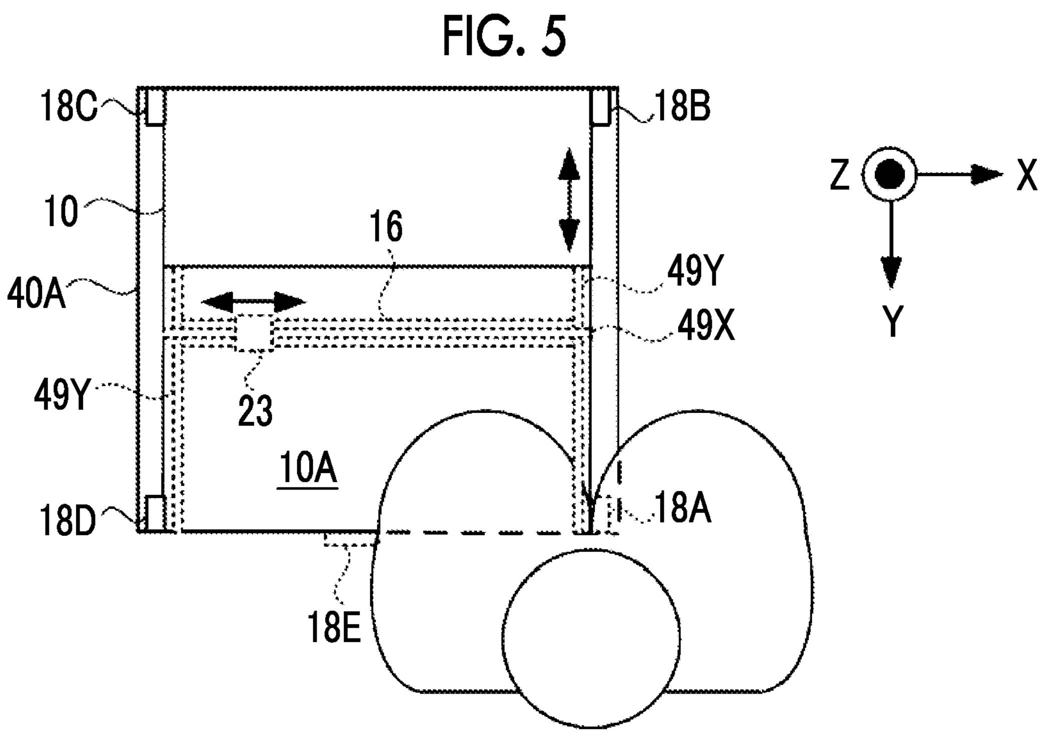
FIG. 5 is a diagram illustrating a state of an examinee placing a breast on a loading surface of an imaging table.

FIG. 5 is a diagram illustrating an example in which an examinee whose a breast is placed on the loading surface 10A is viewed from a position facing the loading surface 10A of the imaging table 10 in the Z-axis direction.

In the example illustrated in FIG. 5, four corners of the side surfaces of the imaging table 10 along the Y-axis direction are fixed to the work table 40A by fixing members 18A, 18B, 18C, and 18D. On the other hand, in addition to the fixing members 18A and 18D for fixing the side surfaces of the imaging table 10 in front of the center of the loading surface 10A, or instead of the fixing members 18A and 18D, the side surface of the imaging table 10 that comes into contact with the chest wall of the examinee may be fixed by the fixing member 18E.

The movement rail 49 is configured with, for example, one movement rail 49X extending along the X-axis direction and two movement rails 49Y extending along the Y-axis direction. The movement rails 49Y are provided along both ends of the loading surface 10A, and the probe driving unit 9 changes a position of the ultrasound probe 23 along the Y-axis direction by moving the movement rail 49X to which the ultrasound probe 23 is attached along the Y-axis direction. In addition, the probe driving unit 9 changes a position of the ultrasound probe 23 along the X-axis direction by moving the ultrasound probe 23 along the movement rail 49X.

Next, a structure of a back surface 10B of the imaging table 10 that is positioned on a side opposite to the loading surface 10A of the imaging table 10 and is in contact with the ultrasonic wave output port of the ultrasound probe 23 will be described.

Figure 6:
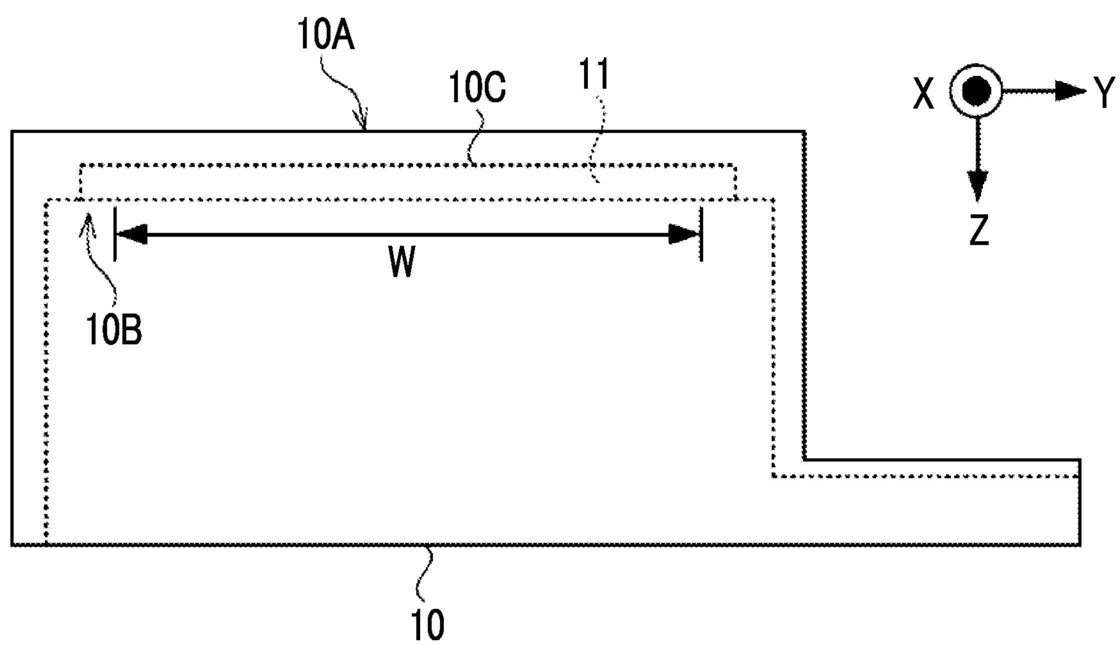
FIG. 6 is a diagram illustrating an example of a structure of the imaging table.

FIG. 6 is a diagram illustrating the side surface of the imaging table 10 attached to the work table 40A along the Y-axis direction in a case of being viewed along the X-axis direction. For convenience of description, in FIG. 6, the fixing member 18, the ultrasound probe 23, the movement rail 49, and the driving members used for moving the ultrasound probe 23, such as the roller 14 and the belt 16, are not illustrated.

A contact surface 10C with an acoustic matching member 11 is present on a back surface 10B of the imaging table 10. The acoustic matching member 11 is a member that is applied between different objects, such as the ultrasound probe 23 and the imaging table 10, and the imaging table 10 and the breast. By applying the acoustic matching member 11 between different objects, a difference in acoustic impedance between different objects is reduced. Specifically, the acoustic matching member 11 is a member that has acoustic impedance close to acoustic impedance of a living body and reduces a difference in acoustic impedance between the breast and the ultrasound probe 23. Thus, the acoustic impedance between the breast and the ultrasound probe 23 is brought close to the acoustic impedance of the living body.

In addition, in a case where a space between the ultrasound probe 23 and the back surface 10B of the imaging table 10 is filled with an acoustic matching member 11 having acoustic impedance close to the acoustic impedance of the living body, air is prevented from being flowed to the space between the ultrasound probe 23 and the back surface 10B, and the ultrasonic wave is more easily transmitted to the breast than in a case where the acoustic matching member is not used. Thus, a clearer ultrasound image can be obtained.

Preferably, a material of the imaging table 10 itself has acoustic impedance close to the acoustic impedance of the living body as possible. For example, polymethylpentene (PMP) is used.

The contact surface 10C on the back surface 10B of the imaging table 10 is recessed with respect to a peripheral surface of the contact surface 10C, and is processed to make it easier to recognize a position where the acoustic matching member 11 is to be applied. The medical worker applies the acoustic matching member 11 to the contact surface 10C recessed from the peripheral surface. In a case where a boundary of the contact surface 10C is in an imaging range W of the ultrasound image, the ultrasound image captured at a boundary portion of the contact surface 10C may be unclearer than the ultrasound image captured at the other portions. For this reason, the boundary of the contact surface 10C is outside the imaging range W of the ultrasound image.

On the back surface 10B of the imaging table 10, the contact surface 10C with the acoustic matching member 11 does not necessarily have to be a surface recessed with respect to a peripheral surface of the contact surface 10C.

Figures 7, 8:
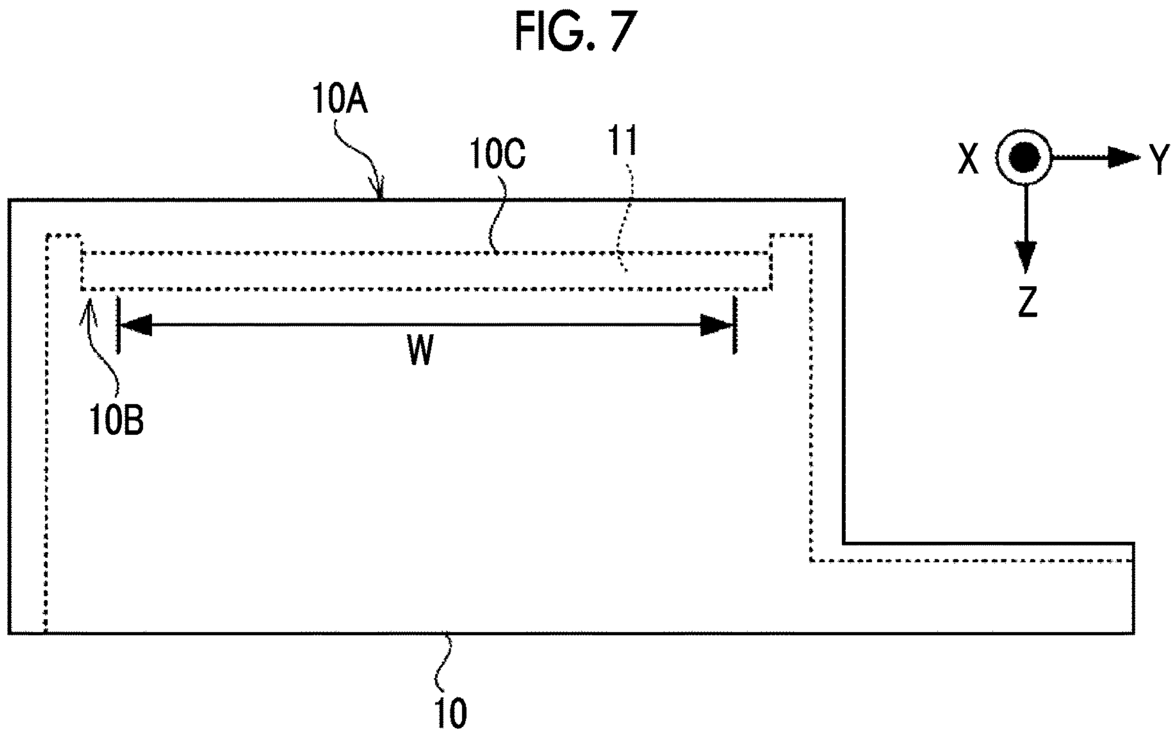
FIG. 7 is a diagram illustrating another example of a structure of the imaging table.
FIG. 8 is a diagram illustrating an example of the imaging table in which jelly is used for an acoustic matching member.

FIG. 7 is a diagram illustrating another example of the shape of the contact surface 10C. The contact surface 10C illustrated in FIG. 7 is protruded from a peripheral surface of the contact surface 10C. The medical worker applies the acoustic matching member 11 to the contact surface 10C that is protruded from the peripheral surface. Even in this case, preferably, the boundary of the contact surface 10C is outside the imaging range W of the ultrasound image.

A type of the acoustic matching member 11 that is in contact with the contact surface 10C is not limited, and for example, a jelly-type acoustic matching member 11 is used. The acoustic matching member 11 may be made of jelly or the like.

In a case where jelly is used as the acoustic matching member 11, the acoustic matching member 11 is fixed to the contact surface 10C by a holding member 13 for attaching the acoustic matching member 11 to the contact surface 10C. For the holding member 13, for example, a double-sided tape is used.

FIG. 8 is a diagram illustrating an example in which jelly which is an example of the acoustic matching member 11 is fixed to the contact surface 10C protruded from the peripheral surface by using the holding member 13. In the example illustrated in FIG. 8, the entire range of the acoustic matching member 11 that is in contact with the contact surface 10C is fixed to the contact surface 10C by using the holding member 13. On the other hand, a part of the range of the acoustic matching member 11 that is in contact with the contact surface 10C may be fixed to the contact surface 10C by using the holding member 13. Of course, the holding member 13 may be used to fix jelly which is an example of the acoustic matching member 11 to the contact surface 10C recessed from the peripheral surface.

Alternatively, the acoustic matching member 11 may be a liquid confined in a sealed bag. In this case, a sealed bag including the liquid acoustic matching member 11 is fixed to the contact surface 10C by using the holding member 13. In a case where a material having adhesiveness is used in a range of the sealed bag that is in contact with the contact surface 10C, the sealed bag can be fixed to the contact surface 10C without using the holding member 13.

Hereinafter, as an example, a description will be given on an assumption that the jelly-type acoustic matching member 11 is applied to the contact surface 10C on the back surface 10B of the imaging table 10. Since the acoustic matching member 11 is applied to the breast, a space between the loading surface 10A of the imaging table 10 and the breast is filled with the acoustic matching member 11.

Figures 9, 10:
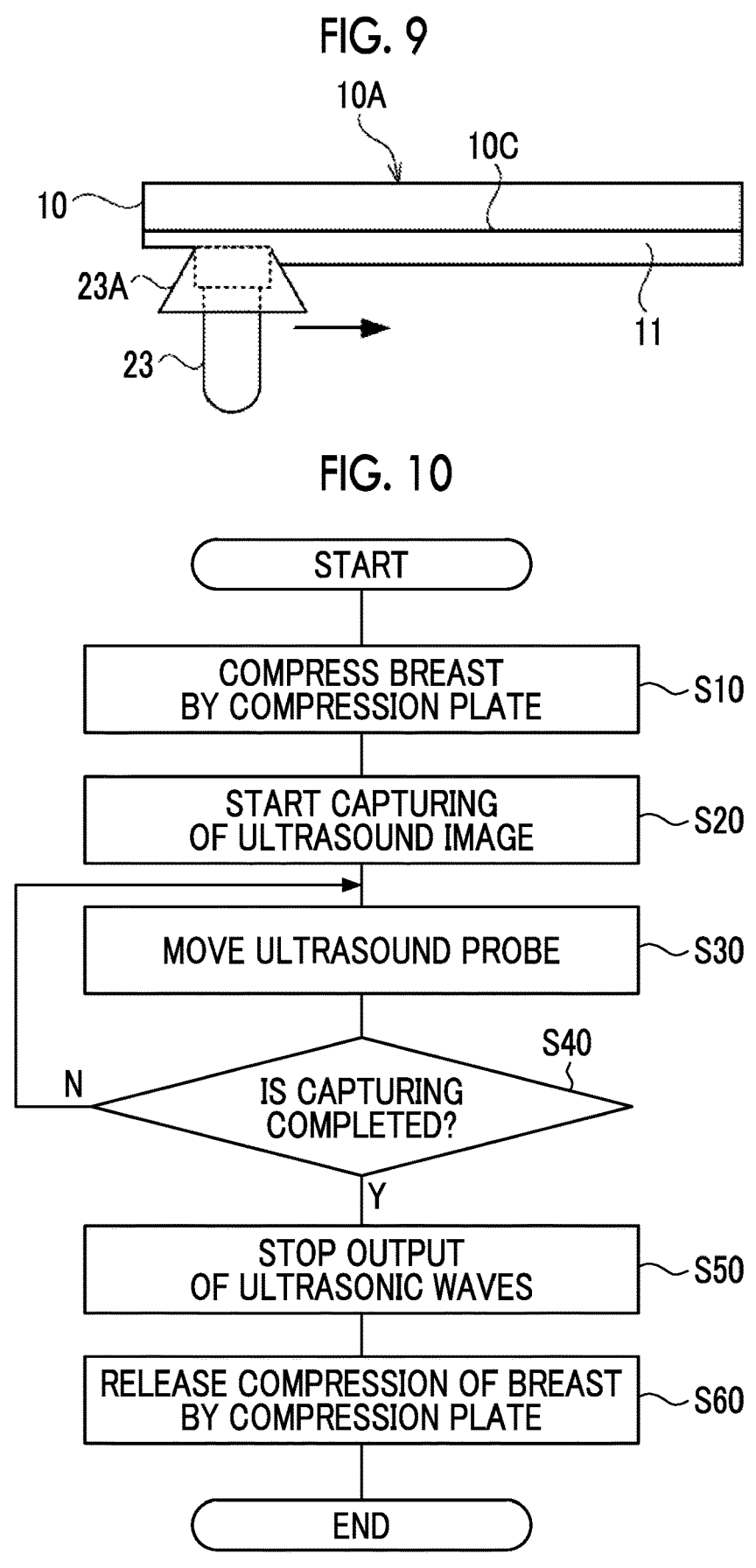

FIG. 9 is a diagram illustrating an example of the ultrasound probe 23 that moves along the back surface 10B of the imaging table 10. A sliding plate 23A is attached to the periphery of the ultrasonic wave output port of the ultrasound probe 23 so as to surround the output port. The sliding plate 23A is a spatula-shaped member that has a role of scraping off the acoustic matching member 11 while spreading the acoustic matching member 11 in the movement direction of the ultrasound probe 23.

In the example of FIG. 9, in order to describe the attachment situation of the sliding plate 23A to the ultrasound probe 23 in an easy-to-understand manner, a portion of the ultrasound probe 23 covered with the sliding plate 23A is indicated by a dotted line. On the other hand, in the ultrasound probe 23 illustrated in other drawings, illustration of the shape of the ultrasound probe 23 covered with the sliding plate 23A is omitted. In addition, illustrations of the movement rail 49 and the driving member such as the roller 14 and the belt 16 used for moving the ultrasound probe 23 are omitted.

Since the jelly-type acoustic matching member 11 is applied to the back surface 10B of the imaging table 10 above the ultrasound probe 23, as the ultrasound probe 23 moves, the acoustic matching member 11 may hang down on the ultrasound probe 23. On the other hand, since the umbrella-shaped sliding plate 23A that covers the periphery of the ultrasound probe 23 is attached to the ultrasound probe 23, the acoustic matching member 11 is prevented from adhering to a main body of the ultrasound probe 23.

Next, an operation of the ultrasonography apparatus 2 that captures an ultrasound image of a breast placed on the loading surface 10A of the imaging table 10 by using the ultrasound probe 23 located in the space below the loading surface 10A of the imaging table 10 will be described.

FIG. 10 is a flowchart illustrating an example of a flow of imaging processing executed by the ultrasonography apparatus 2 in a case where an instruction to start capturing of an ultrasound image of the breast is received according to an operation of a medical worker via the operation unit 27. The CPU 20A of the ultrasonography apparatus 2 reads the control program 21 from the ROM 20B and executes imaging processing.

It is assumed that the acoustic matching member 11 is applied to the breast of the examinee and the contact surface 10C on the back surface 10B of the imaging table 10 prior to capturing of an ultrasound image. The application of the acoustic matching member 11 to the breast may be performed by a medical worker by hand, or may be performed by using an application unit that automatically applies the acoustic matching member 11 to the breast by the ultrasonography apparatus 2. In addition, as illustrated in FIG. 4, a state is assumed in which the examinee places the breast which is the subject on the loading surface 10A of the imaging table 10.

First, in step S10, the controller 20 moves the compression plate 47 in the compression direction and compress the breast by the compression plate 47 by controlling the compression plate driving unit 46 via the compression plate driving section 28.

In step S20, the controller 20 starts capturing of an ultrasound image of the breast by causing the ultrasound probe 23 to output an ultrasonic wave by controlling the ultrasound probe 23 via the probe driving section 22.

In step S30, the controller 20 moves the ultrasound probe 23 to a designated position in a state where the ultrasound probe 23 is in contact with the back surface 10B of the imaging table 10 via the acoustic matching member 11 by controlling the motor via the probe driving section 22. Accordingly, the controller 20 can capture ultrasound images in a continuous range.

In step S40, the controller 20 determines whether or not capturing of ultrasound images in the entire scheduled range is completed. In a case where the capturing is not yet completed, the process proceeds to step S30, and processing of moving the ultrasound probe 23 to the designated position is repeatedly executed.

On the other hand, in a case where it is determined by the determination processing of step S40 that capturing of ultrasound images is completed, the process proceeds to step S50.

As described above, since the ultrasound image of the breast is captured, in step S50, the controller 20 stops the output of the ultrasonic waves by controlling the ultrasound probe 23 via the probe driving section 22.

In step S60, the controller 20 moves the compression plate 47 in the compression release direction and releases compression of the breast by the compression plate 47 by controlling the compression plate driving unit 46 via the compression plate driving section 28. In this way, the imaging processing illustrated in FIG. 10 is ended.

As described above, in the ultrasonography apparatus 2 according to the first embodiment, the imaging table 10 to which the acoustic matching member 11 is applied is attached to the back surface 10B which is the back side of the loading surface 10A of the breast. The ultrasonography apparatus 2 captures an ultrasound image of the breast placed on the loading surface 10A from below the loading surface 10A by using the ultrasound probe 23 in the space below the loading surface 10A.

Modification Example 1 of First Embodiment

Figure 11:
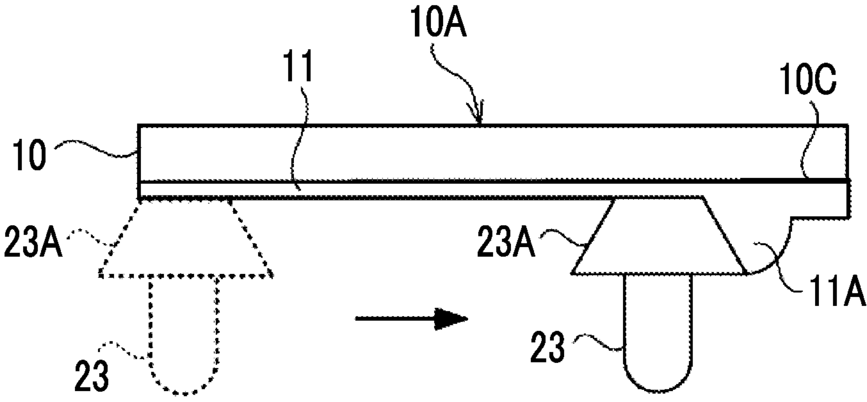
FIG. 11 is a diagram illustrating an example of generation of an acoustic matching member pool according to movement of the ultrasound probe.

FIG. 11 is a diagram illustrating a movement example in which the ultrasound probe 23 is moved from a start point to an end point by the processing of step S30. The start point is an example of a first point, and the end point is an example of a second point.

The sliding plate 23A scrapes off the acoustic matching member 11 while spreading the acoustic matching member 11 in the movement direction of the ultrasound probe 23. Therefore, the acoustic matching member 11 is accumulated on the sliding plate 23A located in front of the ultrasound probe 23 in the movement direction, and thus an acoustic matching member pool 11A is formed.

Therefore, an amount of the acoustic matching member 11 that is applied to the back surface 10B of the imaging table 10 and is located on the movement path of the ultrasound probe 23 is reduced as compared with an amount of the acoustic matching member before movement of the ultrasound probe 23. In a case where an amount of the acoustic matching member 11 applied to the back surface 10B of the imaging table 10 is reduced, for example, air bubbles are likely to be included in the acoustic matching member 11. In a case where air bubbles are generated in the acoustic matching member 11, the acoustic impedance changes at a portion where the air bubbles are generated, and this may cause the ultrasound image to become unclear.

In the present modification example 1, even in a case where the ultrasound probe 23 is moved in a state of being in contact with the back surface 10B of the imaging table 10, a method of moving the ultrasound probe 23 such that reduction of the amount of the acoustic matching member 11 applied to the back surface 10B of the imaging table 10 is prevented will be described.

Figure 12:
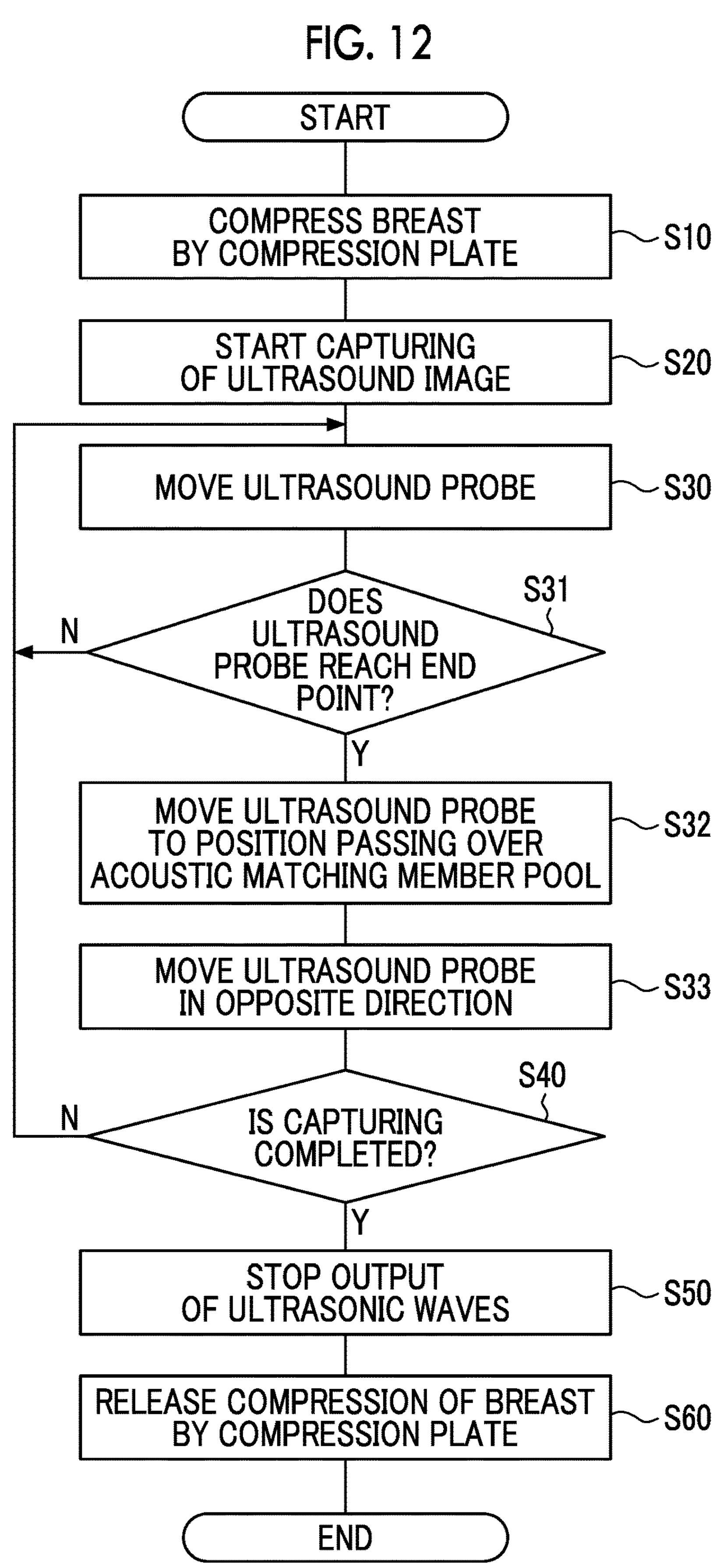
FIG. 12 is a flowchart illustrating an example of a flow of imaging processing of eliminating generation of an acoustic matching member pool.

FIG. 12 is a flowchart illustrating an example of a flow of imaging processing executed by the ultrasonography apparatus 2 according to the present modification example 1 in a case where an instruction to start capturing of an ultrasound image of the breast is received according to an operation of a medical worker via the operation unit 27.

The imaging processing illustrated in FIG. 12 is different from the imaging processing illustrated in FIG. 10 in that step S31 to step S33 are added, and the other processing is the same. Thus, here, the imaging processing illustrated in FIG. 12 will be described mainly with reference to the added processing.

In the present modification example 1, a movement mechanism for moving the ultrasound probe 23 in the space of the imaging table 10 in the Z-axis direction in addition to the X-axis direction and the Y-axis direction is provided.

After the ultrasound probe 23 is moved by the processing of step S30, step S31 is executed.

In step S31, the controller 20 determines whether or not the ultrasound probe 23 reaches the end point. In a case where the ultrasound probe 23 does not reach the end point, the process proceeds to step S30, and the controller 20 continues to move the ultrasound probe 23 by continuously controlling the motor via the probe driving section 22.

On the other hand, in a case where it is determined by the determination processing of step S31 that the ultrasound probe 23 reaches the end point, the processing proceeds to step S32.

In step S32, the controller 20 moves the ultrasound probe 23 in a direction away from the back surface 10B of the imaging table 10 by controlling the motor via the probe driving section 22, and separates the ultrasonic wave output port of the ultrasound probe 23 that reaches the end point away from the back surface 10B of the imaging table 10.

In this case, the controller 20 moves the ultrasound probe 23 to a position where the ultrasonic wave output port passes over the acoustic matching member pool 11A formed by the movement of the ultrasound probe 23.

The controller 20 further moves the ultrasound probe 23, which is moved in a direction away from the back surface 10B of the imaging table 10, along a movement direction from the start point to the end point, and then brings the ultrasonic wave output port into contact with the back surface 10B of the imaging table 10 by moving the ultrasound probe 23 in a direction closer to the back surface 10B of the imaging table 10. Thereby, the ultrasound probe 23 moves to a position passing over the generated acoustic matching member pool 11A.

In step S33, the controller 20 moves the ultrasound probe 23 along the original movement path along which the ultrasound probe 23 is moved from the start point to the end point, in the opposite direction from the end point to the start point in this time by controlling the motor via the probe driving section 22.

Figure 13:
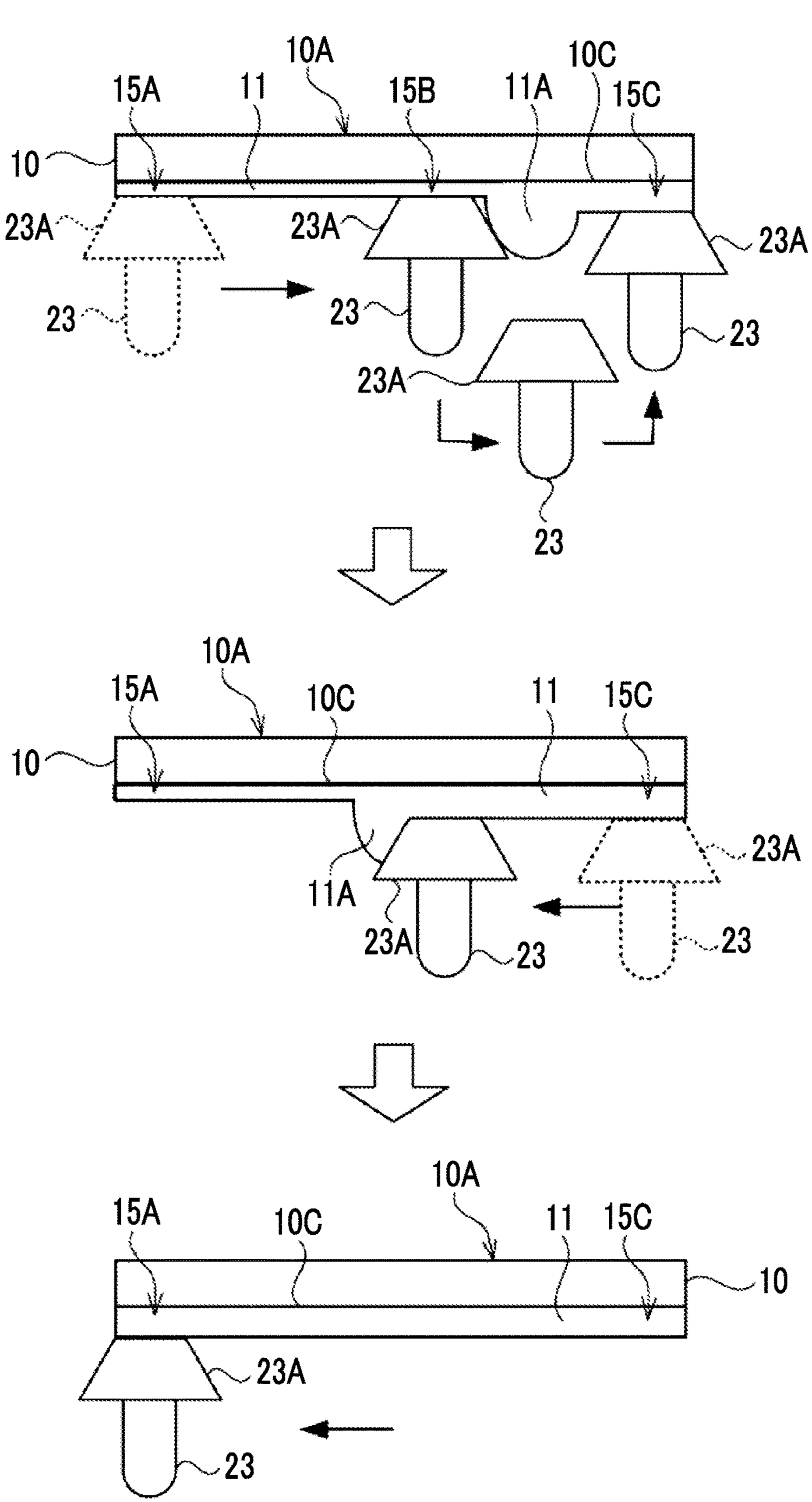
FIG. 13 is a diagram illustrating an example of movement of the ultrasound probe so as to eliminate generation of an acoustic matching member pool.

FIG. 13 is a diagram illustrating a movement example of the ultrasound probe 23 by the imaging processing illustrated in FIG. 12. A position 15A is the start point before movement of the ultrasound probe 23, and a position 15B is the end point of the ultrasound probe 23. A position 15C is a position passing over the acoustic matching member pool 11A.

After the ultrasound probe 23 is moved from the position 15A to the position 15B, the ultrasound probe 23 moves to the position 15C passing over the generated acoustic matching member pool 11A. In a case where the ultrasound probe 23 is moved from the position 15C to the position 15A along the original movement path in a state where the ultrasound probe 23 is in contact with the back surface 10B of the imaging table 10, it can be seen that the acoustic matching member pool 11A is spread out on the movement path along the movement direction and the acoustic matching member 11 is replenished on the original movement path. Therefore, reduction of the amount of the acoustic matching member 11 on the movement path of the ultrasound probe 23 is prevented.

Modification Example 2 of First Embodiment

In the above description, the example in which the ultrasound image of the entire breast is captured while the ultrasound probe 23 is caused to perform scanning along the back surface 10B in a state where the ultrasound probe 23 is in contact with the back surface 10B of the imaging table 10 has been described.

On the other hand, in some situations, it may be desired to capture an ultrasound image of only a specific position of the breast instead of capturing an ultrasound image of the entire breast.

Figure 14:
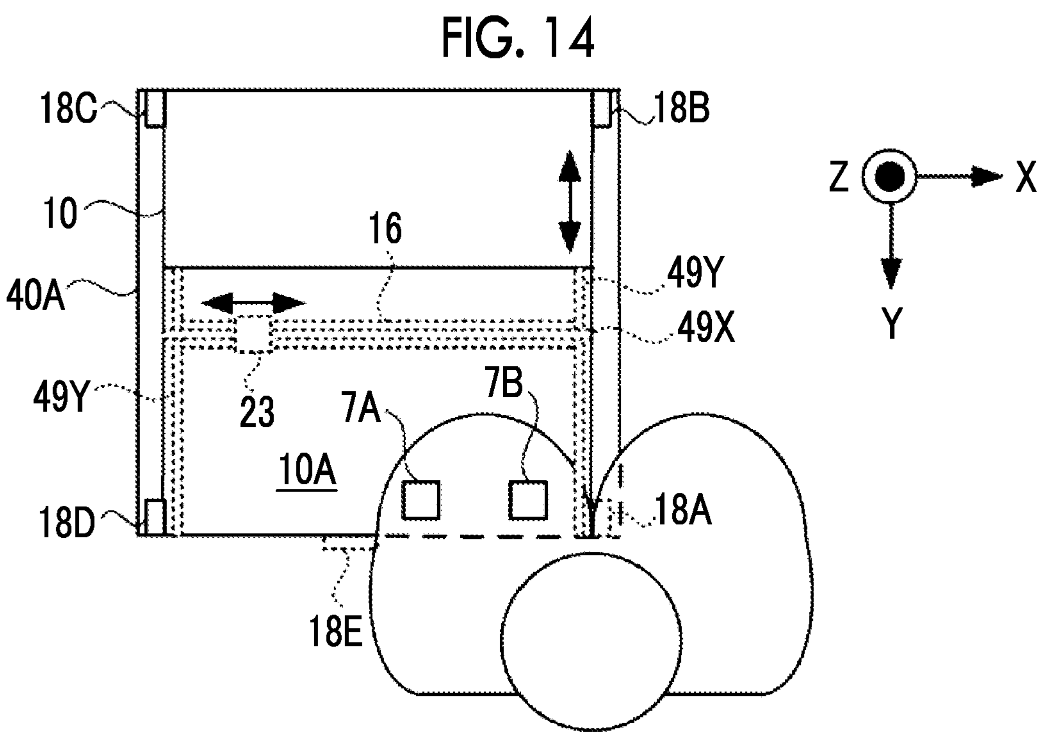
FIG. 14 is a diagram illustrating an example of a specific position of the breast.

FIG. 14 is a diagram illustrating an example in which an examinee whose a breast is placed on the loading surface 10A is viewed from a position facing the loading surface 10A of the imaging table 10 in the Z-axis direction. In FIG. 14, ranges 7A and 7B correspond to positions where it is desired to capture ultrasound images.

In order to support this imaging form, the ultrasonography apparatus 2 according to the present modification example 2 captures an ultrasound image at a specific position of the breast designated in advance, by using the ultrasound probe 23 that is expandable and contractible in the Z-axis direction.

Figure 15:
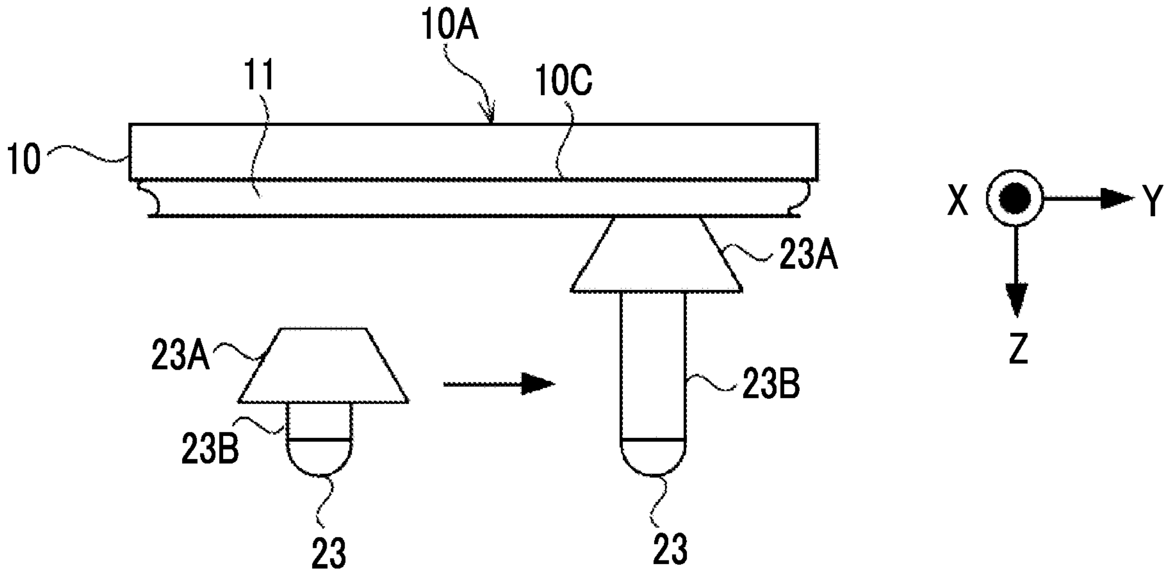
FIG. 15 is a diagram illustrating an example of an ultrasound probe that is expandable and contractible.

FIG. 15 is a diagram illustrating an example of the ultrasound probe 23 that expands and contracts in the Z-axis direction. The ultrasound probe 23 includes an expandable/contractible member 23B, and has a function of expanding and contracting in the Z-axis direction according to an instruction from the probe driving section 22. The controller 20 adjusts a length of the ultrasound probe 23 by controlling a length of the expandable/contractible member 23B via the probe driving section 22.

In the following description, a state where the expandable/contractible member 23B is contracted such that the ultrasonic wave output port of the ultrasound probe 23 does not come into contact with the back surface 10B of the imaging table 10 is referred to as "the ultrasound probe 23 is contracted". In addition, a state where the expandable/contractible member 23B is expanded such that the ultrasonic wave output port of the ultrasound probe 23 comes into contact with the back surface 10B of the imaging table 10 is referred to as "the ultrasound probe 23 is expanded".

Figure 16:
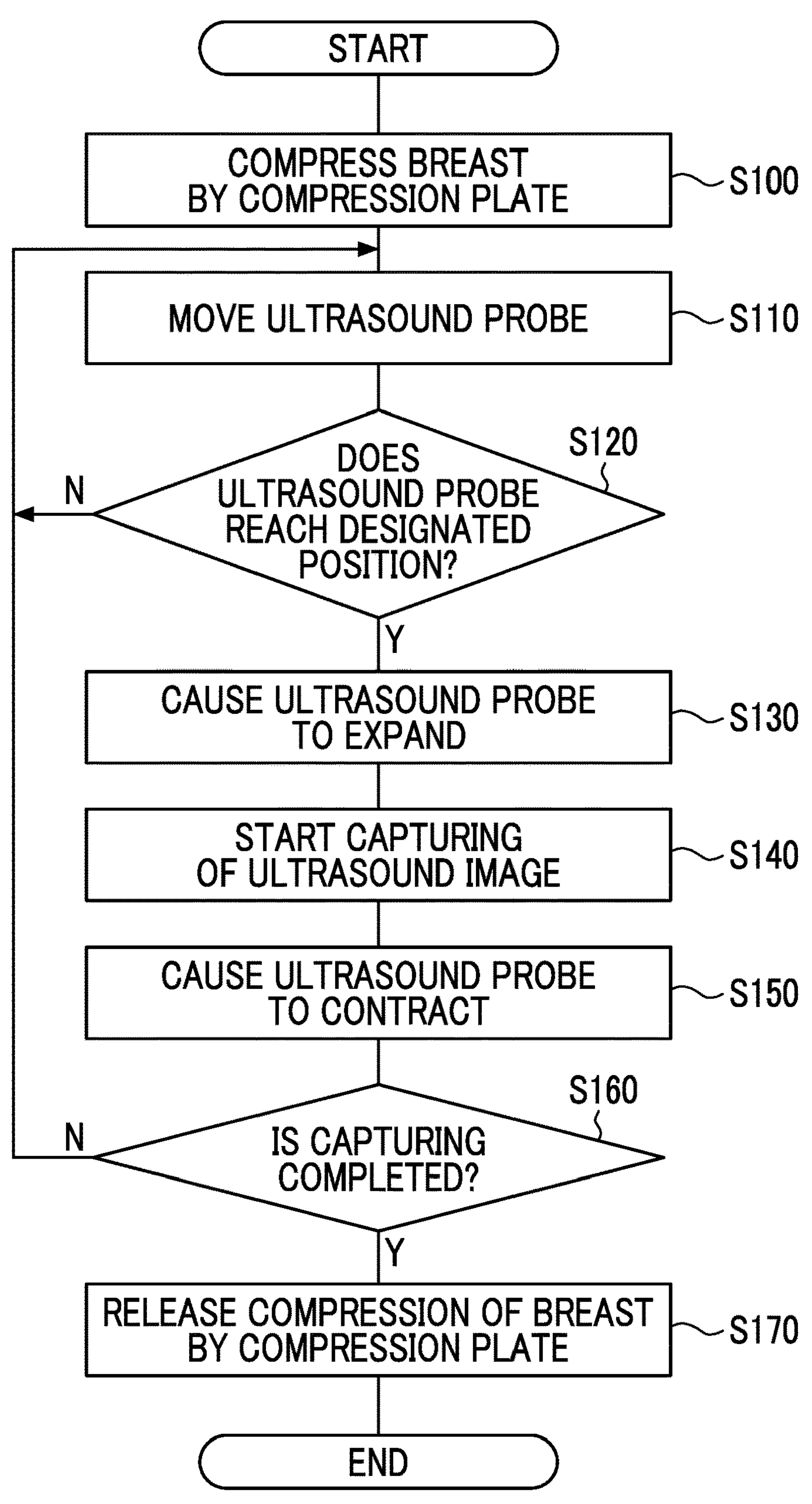
FIG. 16 is a flowchart illustrating an example of a flow of imaging processing of imaging a specific position of the breast.

FIG. 16 is a flowchart illustrating an example of a flow of imaging processing executed by the ultrasonography apparatus 2 according to the present modification example 2 in a case where an instruction to start capturing of an ultrasound image of a designated specific position of the breast is received according to an operation of a medical worker via the operation unit 27.

The CPU 20A of the ultrasonography apparatus 2 reads the control program 21 from the ROM 20B and executes imaging processing illustrated in FIG. 16. It is assumed that the ultrasound probe 23 is contracted at a time when an instruction to start capturing of an ultrasound image is received.

In step S100, the controller 20 moves the compression plate 47 in the compression direction and compress the breast by the compression plate 47 by controlling the compression plate driving unit 46 via the compression plate driving section 28.

In step S110, the controller 20 moves the ultrasound probe 23 in a contracted state to a designated position by controlling the motor via the probe driving section 22.

In step S120, the controller 20 determines whether or not the ultrasound probe 23 reaches the designated position. In a case where the ultrasound probe 23 does not reach the designated position, the process proceeds to step S110, and the controller 20 moves the ultrasound probe 23 to the designated position.

On the other hand, in a case where it is determined by the determination processing of step S120 that the ultrasound probe 23 reaches the designated position, the process proceeds to step S130.

In step S130, the controller 20 causes the ultrasound probe 23 to expand by controlling the ultrasound probe 23 via the probe driving section 22.

In step S140, the controller 20 starts capturing of an ultrasound image of the breast by causing the ultrasound probe 23 to output an ultrasonic wave by controlling the ultrasound probe 23 via the probe driving section 22. That is, the ultrasonography apparatus 2 captures an ultrasound image at the designated specific position of the breast. The controller 20 stops the output of the ultrasonic wave from the ultrasound probe 23 after capturing of the ultrasound image is ended.

In step S150, the controller 20 causes the ultrasound probe 23 to contract by controlling the ultrasound probe 23 via the probe driving section 22.

In step S160, the controller 20 determines whether or not capturing of ultrasound images at all the designated positions is completed. In a case where a position at which capturing is not completed is present, the process proceeds to step S110, and processing of moving the ultrasound probe 23 to the designated position is repeatedly executed.

On the other hand, in a case where it is determined by the determination processing of step S160 that capturing of ultrasound images at all the designated positions is completed, the process proceeds to step S170.

In step S170, the controller 20 moves the compression plate 47 in the compression release direction and releases compression of the breast by the compression plate 47 by controlling the compression plate driving unit 46 via the compression plate driving section 28. In this way, the imaging processing illustrated in FIG. 16 is ended.

As described above, the ultrasonography apparatus 2 according to the present modification example 2 can capture an ultrasound image at a position designated by the medical worker.

Even in the ultrasound probe 23 that does not include the expandable/contractible member 23B, in a case where a movement mechanism for moving the ultrasound probe 23 in the Z-axis direction in addition to the X-axis direction and the Y-axis direction is prepared, the controller 20 can move the ultrasound probe 23 itself in a direction closer to the back surface 10B of the imaging table 10 or in a direction away from the back surface 10B of the imaging table 10 by controlling the probe driving section 22.

Modification Example of Imaging Table 10

In the above description, under the control from the controller 20, by using the ultrasound probe 23 provided with a movement mechanism for moving the ultrasound probe 23 in the space below the loading surface 10A, an ultrasound image of the breast is captured from below the loading surface 10A of the imaging table 10. On the other hand, the controller 20 does not necessarily control the movement of the ultrasound probe 23, and the medical worker may manually move the ultrasound probe 23. In this case, in the space below the loading surface 10A of the imaging table 10, the movement rail 49 and the driving members such as the roller 14 and the belt 16 used for moving the ultrasound probe 23 are unnecessary. Instead, an opening portion 17 for allowing the medical worker to insert a hand holding the ultrasound probe 23 below the loading surface 10A of the imaging table 10 is provided on the side surface of the imaging table 10.

Figure 17:
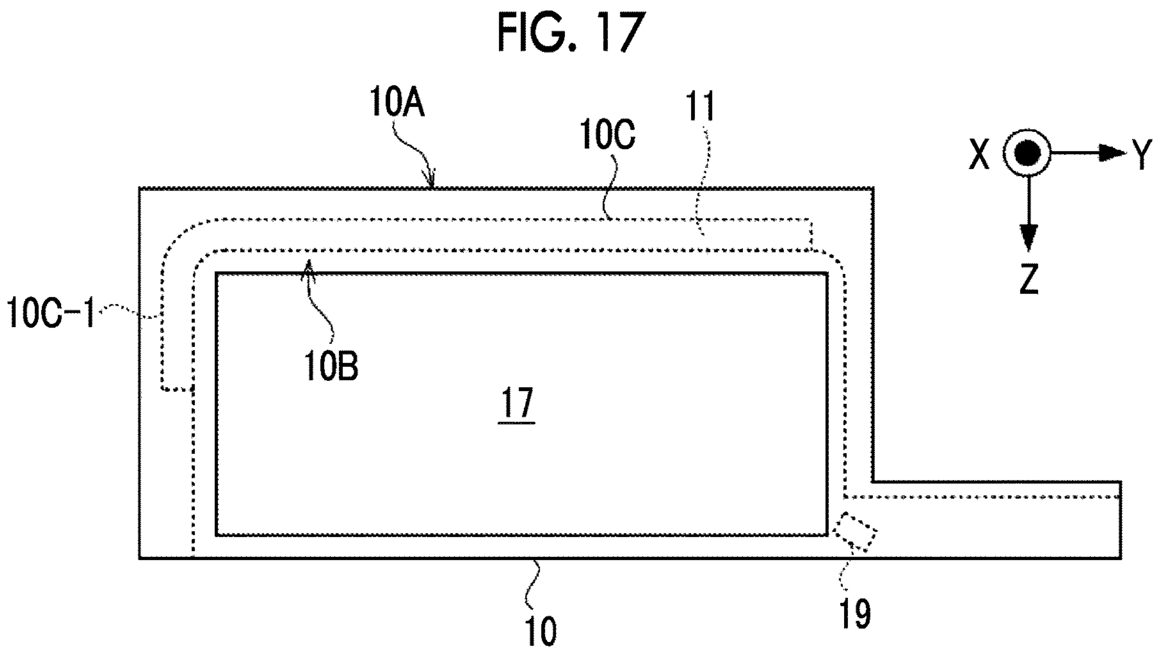
FIG. 17 is a diagram illustrating an example of a structure of an imaging table provided with an opening portion.

FIG. 17 is a diagram of the side surface of the imaging table 10 provided with the opening portion 17 along the Y-axis direction in a case of being viewed in the X-axis direction. For convenience of description, illustration of the fixing member 18 for fixing the imaging table 10 to the work table 40A is omitted.

The opening portion 17 is provided at, among the side surfaces of the imaging table 10, at least one of the side surface in contact with the chest wall or the side surface intersecting with the chest wall, that is, at least one of the side surfaces along the YZ plane. The imaging table 10 illustrated in FIG. 17 has a configuration in which the contact surface 10C is extended not only to the back side of the loading surface 10A but also to the back side of the side surface that comes into contact with the chest wall such that the ultrasound image on the chest wall side of the examinee can be captured. With the configuration, a chest-wall-side contact surface 10C-1 is formed. The acoustic matching member 11 is applied to the contact surface 10C and the chest-wall-side contact surface 10C-1.

The contact surface 10C on the back side of the loading surface 10A and the chest-wall-side contact surface 10C-1 are connected by a curved surface having a predetermined curvature radius. Therefore, the ultrasound probe 23 is easily brought into close contact with the connection portion between the contact surface 10C and the chest-wall-side contact surface 10C-1 as compared with a case where the contact surface 10C and the chest-wall-side contact surface 10C-1 intersect at a right angle. Thus, clear ultrasound images can be captured.

As described above, in a case where the medical worker puts his/her hand from the opening portion 17 to move the ultrasound probe 23, it is difficult for the medical worker to visually observe the position of the ultrasound probe 23. Therefore, a camera 19 that images the ultrasound probe 23 moving in the space is provided in the space of the imaging table 10.

The camera 19 is attached to a position where the entire contact surface 10C and the entire chest-wall-side contact surface 10C-1 of the imaging table 10 can be imaged. Specifically, the camera 19 is attached at a position where the contact surface 10C and the chest-wall-side contact surface 10C-1 of the imaging table 10 are viewed.

The image captured by the camera 19 is displayed on a display by the control of the output unit 26 by the controller 20. By viewing the image displayed on the display, the medical worker can perform capturing of an ultrasound image while confirming the position of the ultrasound probe 23. The number of the cameras 19 is not limited, and the position of the ultrasound probe 23 may be imaged by a plurality of cameras 19. The camera 19 is an example of an imaging device that images the ultrasound probe 23 inserted into the space of the imaging table 10.

As illustrated in FIG. 5, in a case where the imaging table 10 is viewed from the examinee whose the breast is placed on the loading surface 10A of the imaging table 10, the side surface of the imaging table 10 in front of the center of the loading surface 10A is fixed by, for example, the fixing members 18A and 18D. Therefore, even in a case where the medical worker presses the ultrasound probe 23 against the connection portion between the contact surface 10C and the chest-wall-side contact surface 10C-1 and performs capturing of an ultrasound image of the breast, the imaging table 10 is not lifted up.

Second Embodiment

In a second embodiment, a medical imaging system 1A in which a radiography system 4 is added to the medical imaging system 1 illustrated in FIG. 1 will be described.

Figure 18:
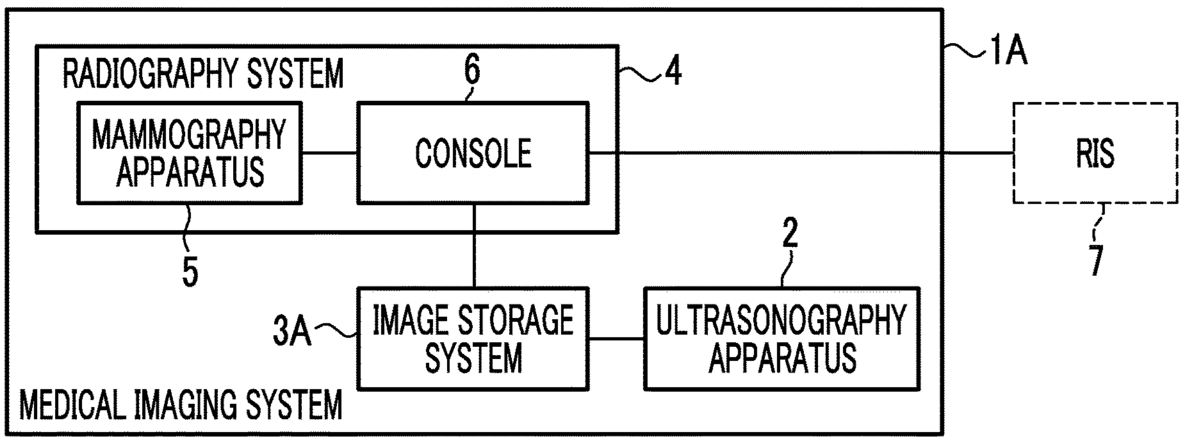
FIG. 18 is a diagram illustrating a configuration example of a medical imaging system according to a second embodiment.

FIG. 18 is a diagram illustrating a configuration example of a medical imaging system 1A according to a second embodiment. The medical imaging system 1A includes the ultrasonography apparatus 2 illustrated in FIG. 1, a radiography system 4, and an image storage system 3A obtained by expanding the image storage system 3 illustrated in FIG. 1. Further, the radiography system 4 includes a mammography apparatus 5 and a console 6.

The mammography apparatus 5 is an apparatus that irradiates a breast of an examinee compressed by the compression plate 47 with radiation R (for example, X-rays: refer to FIG. 20) and captures a radiation image of the breast. The mammography apparatus 5 is realized by a housing common to the ultrasonography apparatus 2 illustrated in FIG. 4. That is, the mammography apparatus 5 also has the functions of the ultrasonography apparatus 2 described in the first embodiment.

The console 6 is an operation console that is used to operate the mammography apparatus 5 and is connected to, for example, the mammography apparatus 5 and the image storage system 3A.

The image storage system 3A is a system that stores ultrasound images captured by the ultrasonography apparatus 2 and radiation images captured by the mammography apparatus 5. The image storage system 3A extracts an ultrasound image and a radiation image corresponding to a request from the console 6 from the stored ultrasound images and the stored radiation images, and transmits the extracted ultrasound image and the extracted radiation image to the console 6.

The console 6 has a function of controlling the mammography apparatus 5 by using a capturing order and various kinds of information acquired from a radiology information system (RIS) 7 via a communication line such as a LAN, an instruction received from the medical worker via the operation unit 27, and the like.

Figure 19:
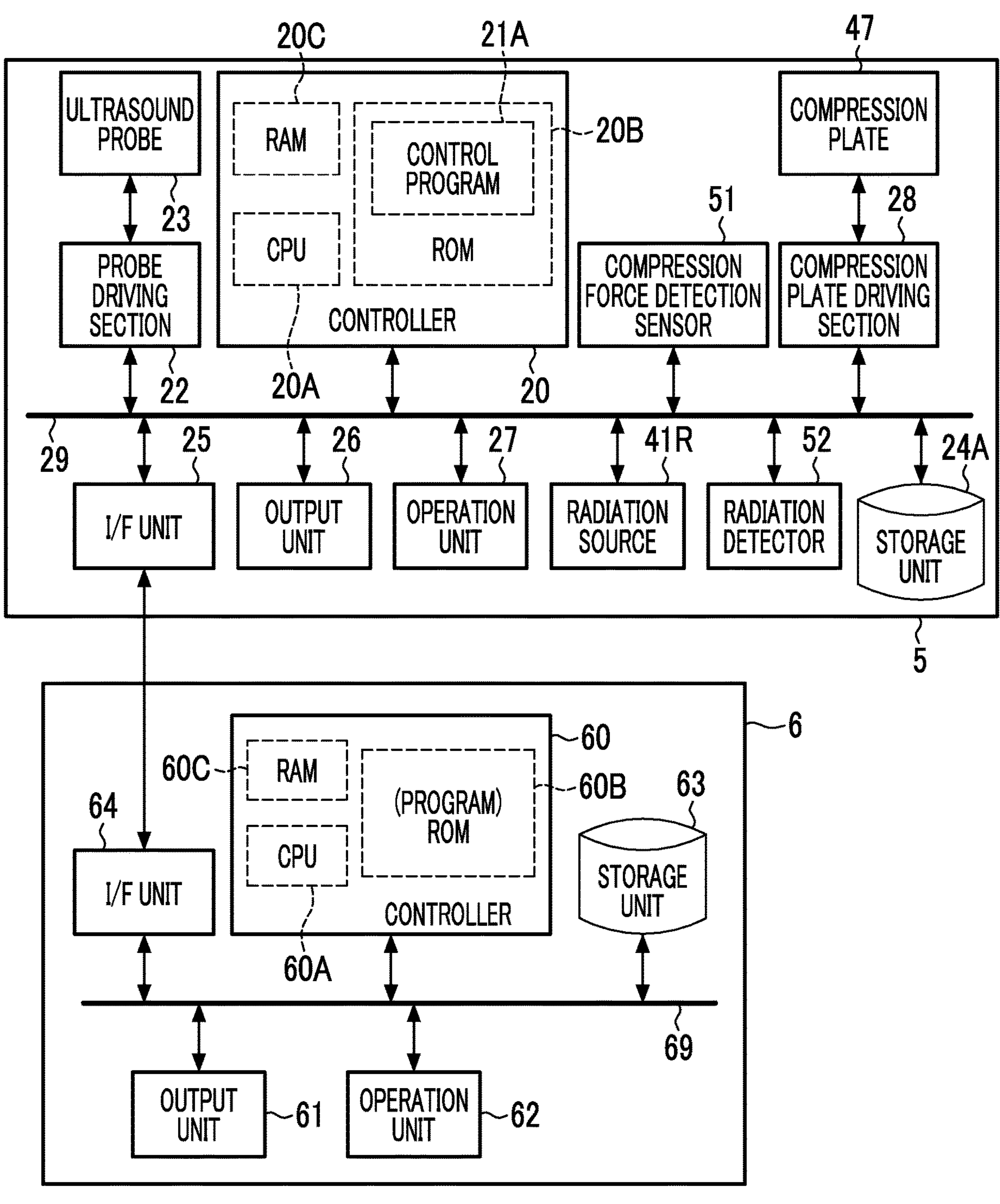
FIG. 19 is a diagram illustrating a configuration example of a mammography apparatus and a console.

FIG. 19 is a diagram illustrating a configuration example of the mammography apparatus 5 and the console 6. The mammography apparatus 5 also has the functions of the ultrasonography apparatus 2. Thus, the mammography apparatus 5 includes, in addition to the configuration of the ultrasonography apparatus 2 illustrated in FIG. 2, a radiation source 41R and a radiation detector 52. In addition, the control program 21 and the storage unit 24 in FIG. 2 are respectively replaced with a control program 21A and a storage unit 24A.

The radiation source 41R irradiates the breast with radiation R under a control of the controller 20 in response to the instruction from the console 6.

The radiation detector 52 is disposed inside the arm portion 42 located below the work table 40A, and detects the radiation R transmitted through the breast which is the subject. The work table 40A irradiated with the radiation R is made of, for example, carbon from the viewpoint of transmittance and intensity of the radiation R.

The storage unit 24A stores the captured ultrasound images, the captured radiation images, various information, and the like.

The compression plate 47 in the mammography apparatus 5 is formed of a material having excellent transmittance for the radiation R. Further, the compression plate 47 is preferably formed of a material that easily propagates the ultrasonic waves output from the ultrasound probe 23. Examples of the material forming the compression plate 47 include resins such as polymethylpentene, polycarbonate, acrylic, and polyethylene terephthalate. In particular, polymethylpentene is suitable as the material forming the compression plate 47 since polymethylpentene has low rigidity, high elasticity, and high flexibility and has suitable values for acoustic impedance that affects the reflectance of ultrasonic waves and an attenuation coefficient that affects the attenuation of ultrasonic waves. The member forming the compression plate 47 is not limited to the above-mentioned example. For example, the member forming the compression plate 47 may be a film-shaped member.

The control program 21A is a program that is read by the CPU 20A, which is an example of a processor, in order to perform control related to the capturing of an ultrasound image and control related to the capturing of a radiation image.

The console 6 is configured by using a server computer as an example. As illustrated in FIG. 19, the console 6 includes a controller 60, an output unit 61, an operation unit 62, a storage unit 63, and an I/F unit 64. The controller 60, the output unit 61, the operation unit 62, the storage unit 63, and the I/F unit 64 are connected to each other via a bus 69 such that various kinds of information can be exchanged.

The controller 60 controls the overall operation of the console 6. The controller 60 includes a CPU 60A, a ROM 60B, and a RAM 60C. Various programs and the like executed by the CPU 60A are stored in the ROM 60B in advance. The RAM 60C is used as a temporary work area of the CPU 60A.

The output unit 61 outputs information processed by the controller 60 to the medical worker.

The operation unit 62 is used by the medical worker to input instructions, various types of information, and the like related to capturing of a radiation image, including an irradiation instruction of the radiation R. Therefore, the operation unit 62 includes at least an irradiation instruction button that is pressed by the medical worker to input an instruction to emit the radiation R. An operation form of the operation unit 62 is not limited, and, for example, an operation by a switch, a touch panel, a touch pen, a mouse, or the like can be received.

The storage unit 63 stores the radiation images captured by the mammography apparatus 5, various kinds of information, and the like. The storage unit 63 is an example of a storage device that maintains stored information even in a case where power supplied to the storage unit 63 is cut off. For example, a semiconductor memory such as an SSD is used, or a hard disk may be used.

The I/F unit 64 transmits and receives various kinds of information to and from the mammography apparatus 5 connected to, for example, a communication line such as LAN, the RIS 7, and the image storage system 3A using wireless communication or wired communication. For example, the console 6 receives a radiation image captured by the mammography apparatus 5 via the I/F unit 64, transmits the received radiation image to the image storage system 3A via the I/F unit 64, and stores the radiation image in the image storage system 3A.

Figure 20:
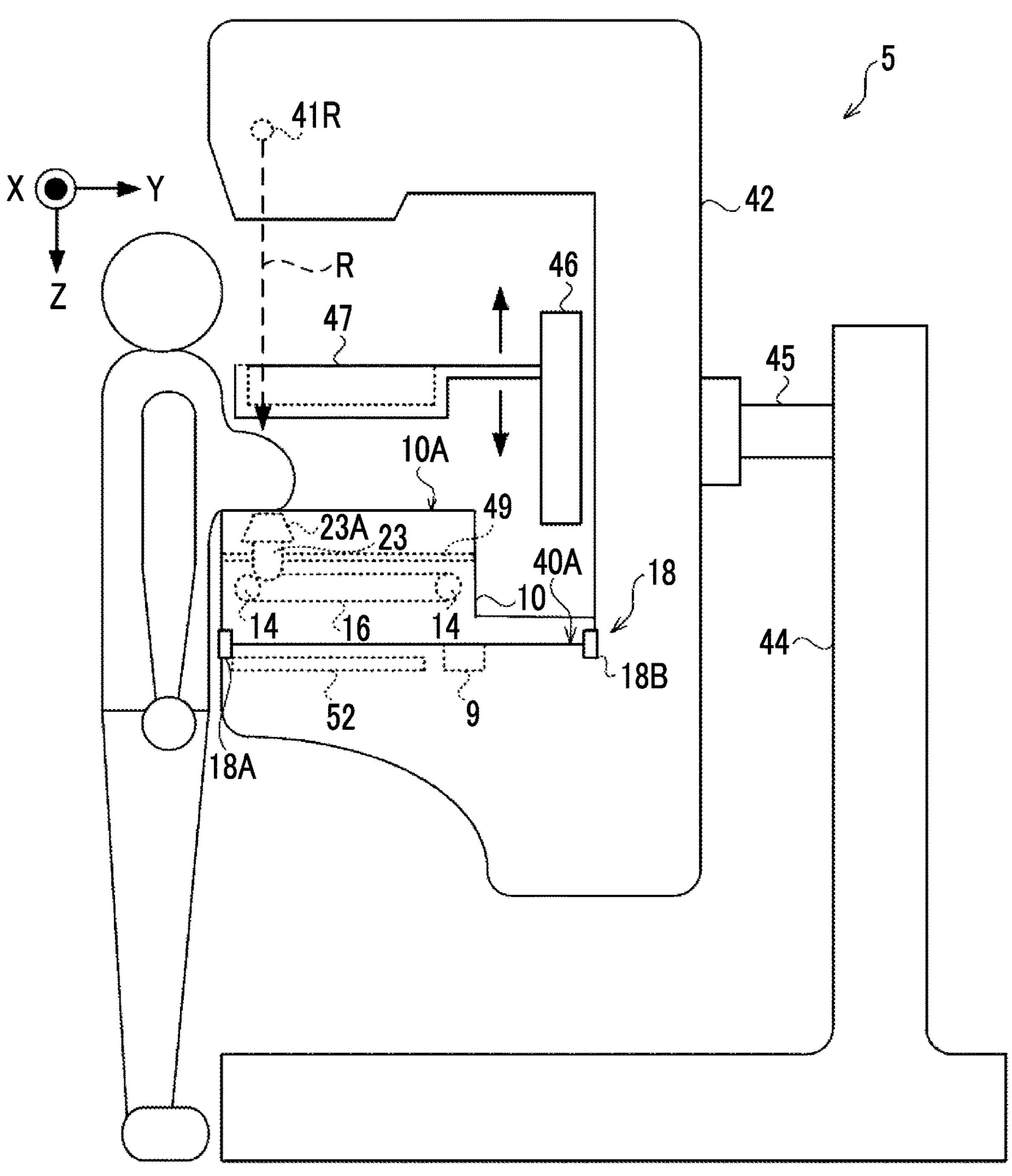
FIG. 20 is a diagram illustrating an example of an external appearance of the ultrasonography apparatus according to the second embodiment.

FIG. 20 is a diagram illustrating an example of an external appearance of the mammography apparatus 5 in a case where the mammography apparatus is viewed from a side. In the mammography apparatus 5 as well, the imaging table 10 is attached to the work table 40A, and an ultrasound image and a radiation image of the breast are captured in a state where the breast of the examinee is placed on the loading surface 10A of the imaging table 10.

In the mammography apparatus 5 illustrated in FIG. 20, the radiation source 41R and the radiation detector 52 are added to the apparatus configuration of the ultrasonography apparatus 2 illustrated in FIG. 4.

The radiation source 41R is provided in the arm portion 42 at a position facing the loading surface 10A of the imaging table 10.

The mammography apparatus 5 can capture an image of the breast of the examinee in a state where the examinee is sitting on a chair (including a wheelchair) or the like (sitting state) in addition to a state where the examinee is standing (standing state).

In addition, for example, a magnification imaging table is used as the imaging table 10 to be attached to the mammography apparatus 5. The magnification imaging table is a table for capturing a radiation image of the breast that is magnified as compared with a case where the breast is directly placed on the work table 40A, by bringing the breast that is the subject close to the radiation source 41R.

Next, an operation of the mammography apparatus 5 that captures an ultrasound image and a radiation image of the breast will be described in detail.

Figure 21:
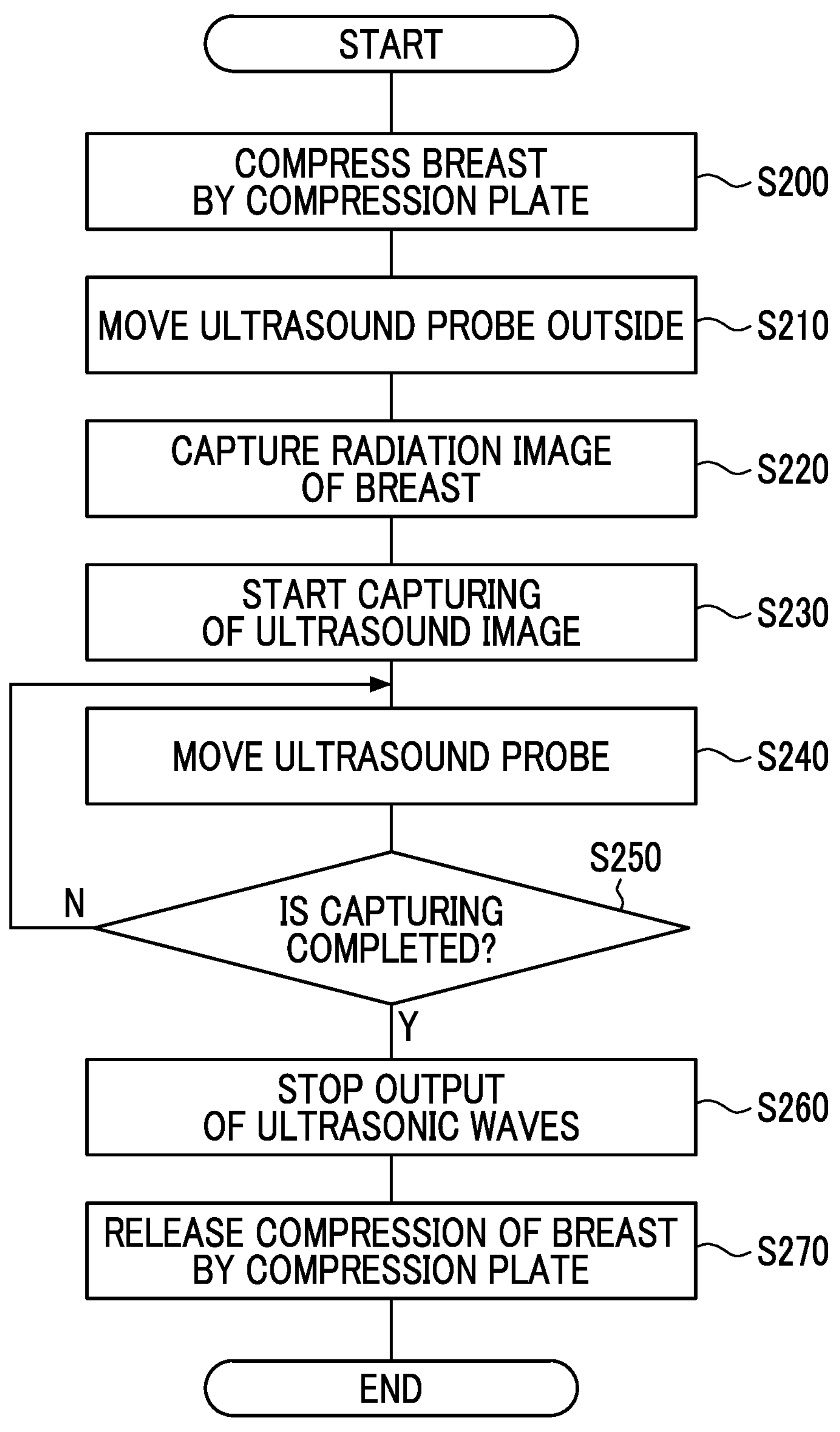
FIG. 21 is a flowchart illustrating an example of a flow of imaging processing executed by the mammography apparatus.

FIG. 21 is a flowchart illustrating an example of a flow of imaging processing executed by the mammography apparatus 5 in a case where an instruction to start capturing of an ultrasound image and a radiation image of the breast is received according to an operation of a medical worker via the console 6. The CPU 20A of the mammography apparatus 5 reads the control program 21A from the ROM 20B and executes imaging processing.

It is assumed that the acoustic matching member 11 is applied to the breast of the examinee and the contact surface 10C on the back surface 10B of the imaging table 10 prior to capturing of an ultrasound image. The application of the acoustic matching member 11 to the breast may be performed by a medical worker by hand, or may be performed by using an application unit that automatically applies the acoustic matching member 11 to the breast. In addition, as illustrated in FIG. 20, a state is assumed in which the examinee places the breast which is the subject on the loading surface 10A of the imaging table 10.

First, in step S200, the controller 20 moves the compression plate 47 in the compression direction and compress the breast by the compression plate 47 by controlling the compression plate driving unit 46 via the compression plate driving section 28.

In step S210, the controller 20 moves the ultrasound probe 23 outside an imaging range of the radiation image such that the presence of the ultrasound probe 23 does not affect the radiation image, by controlling the motor via the probe driving section 22. For example, position information indicating a position outside the imaging range of the radiation image is stored in advance in the ROM 20B. The capturing of the radiation image is an example of capturing other than capturing of an ultrasound image.

Figure 22:
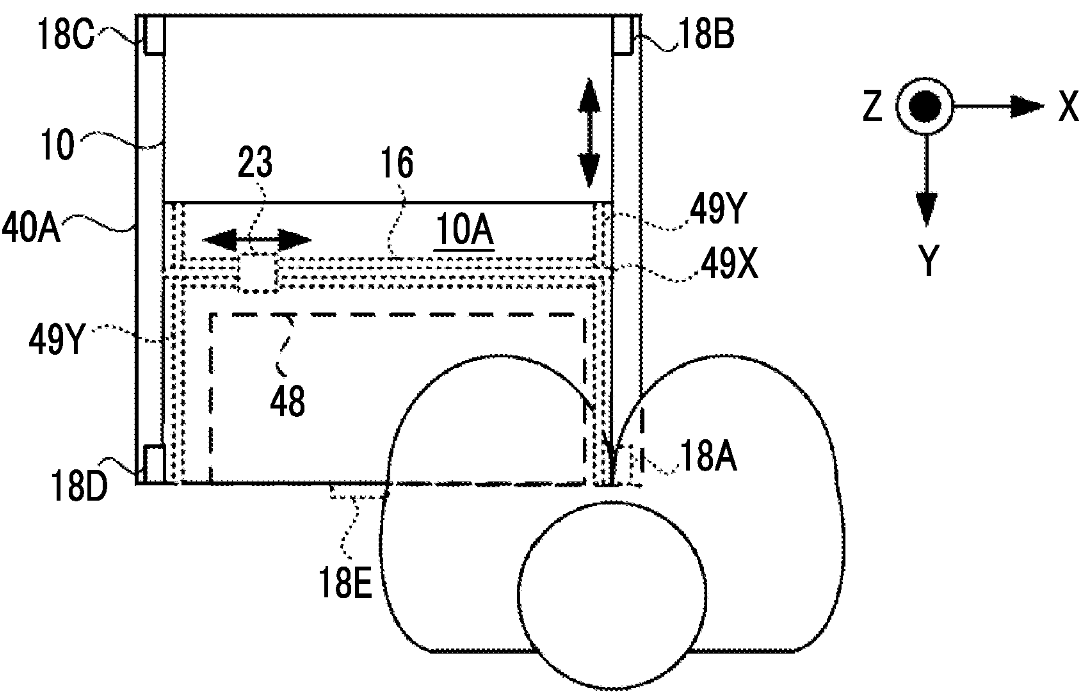
FIG. 22 is a diagram illustrating an example of an ultrasound probe that is moved outside an imaging range of a radiation image.

FIG. 22 is a diagram illustrating a state where the ultrasound probe 23 is moved outside the imaging range of the radiation image. By processing of step S210, the ultrasound probe 23 is moved to a position outside the imaging range 48 of the radiation image.

In step S220, the controller 20 controls the radiation source 41R to start emission of radiation R, and captures a radiation image of the breast compressed by the compression plate 47.

In step S230, the controller 20 starts capturing of an ultrasound image of the breast by causing the ultrasound probe 23 to output an ultrasonic wave by controlling the ultrasound probe 23 via the probe driving section 22.

In step S240, the controller 20 moves the ultrasound probe 23 to a designated position in a state where the ultrasound probe 23 is in contact with the back surface 10B of the imaging table 10 via the acoustic matching member 11 by controlling the motor via the probe driving section 22.

In step S250, the controller 20 determines whether or not capturing of ultrasound images in the entire scheduled range is completed. In a case where the capturing is not yet completed, the process proceeds to step S240, and processing of moving the ultrasound probe 23 to the designated position is repeatedly executed.

On the other hand, in a case where it is determined by the determination processing of step S250 that capturing of ultrasound images is completed, the process proceeds to step S260.

As described above, since the ultrasound image of the breast is captured, in step S260, the controller 20 stops the output of the ultrasonic waves by controlling the ultrasound probe 23 via the probe driving section 22.

In step S270, the controller 20 moves the compression plate 47 in the compression release direction and releases compression of the breast by the compression plate 47 by controlling the compression plate driving unit 46 via the compression plate driving section 28. In this way, the imaging processing illustrated in FIG. 21 is ended.

In the processing of step S240, the medical worker may hold the ultrasound probe 23 in his/her hand, bring the ultrasound probe 23 close to the breast through the compression plate 47, and capture an ultrasound image of an upper side of the breast.

In addition, the controller 20 may specify, from the radiation image of the breast, a portion that is considered to be preferably examined in more detail by ultrasonic waves, and may capture ultrasound images only at the specified portion of the breast. The controller 20 performs diagnosis of the radiation image using, for example, a diagnosis method using a computer, such as computer-aided diagnosis (CAD).

As described above, the mammography apparatus 5 performs capturing of an ultrasound image of the breast in addition to capturing of a radiation image of the breast. In addition, by using the imaging table 10, the mammography apparatus 5 can capture an ultrasound image of a lower side of the breast. In addition to the imaging table 10 that accommodates the movement rail 49 and the driving members such as the roller 14 and the belt 16 used for moving the ultrasound probe 23, the imaging table 10 may be an imaging table 10 configured such that a medical worker manually moves the ultrasound probe 23 as illustrated in FIG. 17.

In addition, the movement control of the ultrasound probe 23 in the imaging processing illustrated in FIG. 12 and FIG. 16 may be applied to the movement of the ultrasound probe 23.

As described above, aspects of the medical imaging systems 1 and 1A have been described using the embodiments. On the other hand, the aspects of the disclosed medical imaging systems 1 and 1A are examples, and the aspects of the medical imaging systems 1 and 1A are not limited to the range described in the embodiments. Various modifications and improvements can be added to the exemplary embodiments without departing from the scope of the present disclosure, and the exemplary embodiments to which the modifications or improvements are added are also included in the technical scope of the present disclosure.

For example, the internal processing order in the flowcharts illustrated in FIG. 10, FIG. 12, FIG. 16, and FIG. 21 may be changed without departing from the spirit of the present disclosure.

In the embodiments, for example, a form in which the imaging processing illustrated in FIG. 10, FIG. 12, FIG. 16, and FIG. 21 is implemented by software processing has been described. On the other hand, processing equivalent to the flowchart of the imaging processing may be performed by hardware. In this case, the processing speed can be increased as compared with a case where the imaging processing is implemented by software processing.

In the embodiments above, the term "processor" refers to hardware in a broad sense. Examples of the processor include general processors (e.g., CPU 20A) and dedicated processors (e.g., GPU: Graphics Processing Unit, ASIC: Application Specific Integrated Circuit, FPGA: Field Programmable Gate Array, and programmable logic device).

Further, the operation of the processor in the embodiments may be performed not only by one processor but also by cooperation of a plurality of processors provided at physically separated positions. Further, the order of the operations of the processor is not limited to only the order described in the embodiments, and may be changed as appropriate.

In the embodiments, examples in which the control programs 21 and 21A are stored in the ROM 20B have been described. On the other hand, the storage destination of the control programs 21 and 21A is not limited to the ROM 20B. The control programs 21 and 21A can also be provided by being recorded in a computer-readable storage medium.

For example, the control programs 21 and 21A may be provided by being recorded on an optical disk, such as a compact disk read only memory (CD-ROM), a digital versatile disk read only memory (DVD-ROM), and a blue ray disk. In addition, the control programs 21 and 21A may be provided by being recorded in a portable semiconductor memory such as a universal serial bus (USB) memory and a memory card. The ROM 20B, the CD-ROM, the DVD-ROM, the blue ray disk, the USB, and the memory card are examples of non-transitory storage media.

Further, the controller 20 may download the control programs 21 and 21A from an external apparatus connected to the communication line via the I/F unit 25 and store the downloaded control programs 21 and 21A in the ROM 20B of the controller 20. In this case, the CPU 20A of the controller 20 reads, from the ROM 20B, the control programs 21 and 21A downloaded from the external apparatus, and executes the imaging processing.

What is claimed is:

1. An ultrasonography apparatus comprising:

an imaging table including:

a loading surface configured to support placement of a breast;

a space that is provided below the loading surface, and that is configured to accommodate an ultrasound probe which outputs an ultrasonic wave from an outside of the loading surface toward the loading surface and acquires a reflected wave of the ultrasonic wave from the breast; and a back surface including:

a recessed portion recessed toward the loading surface; and a peripheral portion surrounding the recessed portion, wherein a bottom surface of the recessed portion defines a contact surface configured to contact with an acoustic matching member which is configured to reduce a difference in acoustic impedance between the breast and the ultrasound probe;

a controller configured to perform control of capturing an ultrasound image using the reflected wave of the ultrasonic wave;

a movement mechanism that is configured to move the ultrasound probe in the space formed by the imaging table, and that includes a movement rail to which the ultrasound probe is attached, and a belt suspended between at least two rollers rotated by a motor; and a sliding plate that is attached to the ultrasound probe, and that is configured to scrape off the acoustic matching member while spreading the acoustic matching member on the back surface in a movement direction of the ultrasound probe, wherein the controller is configured to cause the movement mechanism to move the ultrasound probe in a state where the ultrasound probe is in contact with the back surface via the acoustic matching member, and wherein the controller is further configured to perform control of:

moving the ultrasound probe from a first point to a second point, the ultrasound probe being in contact with the back surface via the acoustic matching member at the second point, separating the ultrasound probe from the back surface at the second point such that the ultrasound probe is not brought into contact with an acoustic matching member pool, the acoustic matching member pool being formed in front of the ultrasound probe in the movement direction by the acoustic matching member being scraped off from the back surface due to movement of the ultrasound probe from the first point to the second point, moving the ultrasound probe to a position passing over the acoustic matching member pool, bringing the ultrasound probe into contact with the back surface, and moving the ultrasound probe toward the first point again.

2. The ultrasonography apparatus according to claim 1, wherein in a case where the acoustic matching member is jelly, the acoustic matching member is fixed to the contact surface by a holding member that attaches the acoustic matching member to the contact surface.

3. The ultrasonography apparatus according to claim 1, wherein in a case where imaging other than capturing of an ultrasound image is performed on the breast placed on the loading surface of the imaging table, the controller performs control of moving the ultrasound probe outside an imaging range of the other imaging.

4. A mammography apparatus comprising:

the ultrasonography apparatus according to claim 1.

5. A non-transitory storage medium storing a program that causes a computer to execute a control process for an ultrasonography apparatus, the ultrasonography apparatus comprising:

an imaging table including:

a loading surface configured to support placement of a breast;

a space that is provided below the loading surface, and that is configured to accommodate an ultrasound probe which outputs an ultrasonic wave from an outside of the loading surface toward the loading surface and acquires a reflected wave of the ultrasonic wave from the breast; and a back surface including:

a recessed portion recessed toward the loading surface; and a peripheral portion surrounding the recessed portion, wherein a bottom surface of the recessed portion defines a contact surface configured to contact with an acoustic matching member which is configured to reduce a difference in acoustic impedance between the breast and the ultrasound probe;

a controller configured to perform control of capturing an ultrasound image using the reflected wave of the ultrasonic wave;

a movement mechanism that is configured to move the ultrasound probe in the space formed by the imaging table, and that includes a movement rail to which the ultrasound probe is attached, and a belt suspended between at least two rollers rotated by a motor; and a sliding plate that is attached to the ultrasound probe, and that is configured to scrape off the acoustic matching member while spreading the acoustic matching member on the back surface in a movement direction of the ultrasound probe, the control process comprising:

processing of performing control to capture the ultrasound image, processing of performing control to cause the movement mechanism to move the ultrasound probe in a state where the ultrasound probe is in contact with the back surface via the acoustic matching member, processing of performing control to move the ultrasound probe from a first point to a second point, the ultrasound probe being in contact with the back surface via the acoustic matching member at the second point, processing of performing control to separate the ultrasound probe from the back surface at the second point such that the ultrasound probe is not brought into contact with an acoustic matching member pool, the acoustic matching member pool being formed in front of the ultrasound probe in the movement direction by the acoustic matching member being scraped off from the back surface due to movement of the ultrasound probe from the first point to the second point, processing of performing control to move the ultrasound probe to a position passing over the acoustic matching member pool, processing of performing control to bring the ultrasound probe into contact with the back surface, and processing of performing control to move the ultrasound probe toward the first point again.

* * * * *